United States Patent
Nishtala et al.

(10) Patent No.: US 9,855,163 B2
(45) Date of Patent: Jan. 2, 2018

(54) WASTE MANAGEMENT SYSTEM

(75) Inventors: Vasu Nishtala, Snellville, GA (US);
Michele Gandy Davis, Forsyth, GA (US); Ronald L. Bracken, Conyers, GA (US); Robert M. Hine, Covington, GA (US)

(73) Assignee: C. R. Bard, Inc., Murray Hill, NJ (US)

( * ) Notice: Subject to any disclaimer, the term of this patent is extended or adjusted under 35 U.S.C. 154(b) by 1092 days.

(21) Appl. No.: 12/434,446

(22) Filed: May 1, 2009

(65) Prior Publication Data

US 2009/0216206 A1    Aug. 27, 2009

Related U.S. Application Data

(62) Division of application No. 12/438,200, filed as application No. PCT/US2007/081120 on Oct. 11, 2007, now Pat. No. 8,926,577.

(60) Provisional application No. 60/958,217, filed on Jul. 3, 2007, provisional application No. 60/829,758, filed on Oct. 17, 2006.

(51) Int. Cl.
*A61M 5/44* (2006.01)
*A61F 5/44* (2006.01)
*A61M 39/10* (2006.01)

(52) U.S. Cl.
CPC .............. *A61F 5/44* (2013.01); *A61F 5/4405* (2013.01); *A61F 5/4408* (2013.01); *A61M 39/10* (2013.01); *A61M 2039/1044* (2013.01)

(58) Field of Classification Search
CPC ........ A61F 5/4408; A61F 5/44; A61F 5/4405; A61M 39/10; A61M 2039/1044

USPC .......................................................... 604/327
See application file for complete search history.

(56) References Cited

U.S. PATENT DOCUMENTS

| | | |
|---|---|---|
| 756,582 A | 4/1904 | Chaplin |
| 1,965,653 A | 7/1934 | Kennedy |
| 2,457,244 A | 12/1948 | Lamson |
| 3,053,257 A | 9/1962 | Birtwell |
| 3,154,077 A | 10/1964 | Cannon |
| 3,217,770 A | 11/1965 | Garth |
| 3,253,593 A | 5/1966 | Cronin |
| 3,306,327 A | 2/1967 | Ilg |
| 3,459,175 A | 8/1969 | Miller |

(Continued)

FOREIGN PATENT DOCUMENTS

| | | |
|---|---|---|
| AU | 2007312985 B2 | 9/2013 |
| CA | 2666631 A1 | 4/2008 |

(Continued)

OTHER PUBLICATIONS

US 8,123,732, 02/2012, Martino et al. (withdrawn)

(Continued)

*Primary Examiner* — Tatyana Zalukaeva
*Assistant Examiner* — Benjamin Klein
(74) *Attorney, Agent, or Firm* — Rutan & Tucker, LLP

(57) ABSTRACT

A waste management system includes a waste transport device and a waste collection device. The waste transport device includes a collection member with a distal end opening having a first cross-sectional area and a proximal end opening having a second cross-sectional area less than the first cross-sectional area, a retention cuff disposed about an outer surface of the collection member, and a first section having a lumen in fluid communication with a lumen of the collection member.

20 Claims, 20 Drawing Sheets

(56) References Cited

U.S. PATENT DOCUMENTS

| | | |
|---|---|---|
| 3,478,743 A | 11/1969 | Ericson |
| 3,506,011 A | 4/1970 | Silverman |
| 3,543,744 A | 12/1970 | LePar |
| 3,548,828 A | 12/1970 | Vasile |
| 3,598,150 A | 8/1971 | Nolan |
| 3,669,099 A | 6/1972 | Silverman |
| 3,750,668 A | 8/1973 | Perl |
| 3,771,522 A | 11/1973 | Waysilk et al. |
| 3,802,418 A | 4/1974 | Clayton |
| 3,828,774 A | 8/1974 | Vass |
| 3,848,602 A | 11/1974 | Gutnick |
| 3,866,601 A | 2/1975 | Russell |
| 3,897,780 A | 8/1975 | Trousil |
| 3,901,235 A | 8/1975 | Patel et al. |
| 3,911,107 A | 10/1975 | Krezanoski |
| 3,931,819 A | 1/1976 | Weedle |
| 3,938,521 A | 2/1976 | Ritota et al. |
| 3,967,645 A | 7/1976 | Gregory |
| 3,983,879 A | 10/1976 | Todd |
| 4,013,077 A | 3/1977 | Ritota et al. |
| 4,016,885 A | 4/1977 | Bruner |
| 4,030,500 A | 6/1977 | Ronnquist et al. |
| 4,055,179 A | 10/1977 | Manschot et al. |
| 4,059,124 A | 11/1977 | Hill |
| 4,067,335 A | 1/1978 | Silvanov |
| 4,117,847 A | 10/1978 | Clayton |
| 4,143,853 A | 3/1979 | Abramson |
| 4,164,795 A | 8/1979 | Johnson |
| 4,182,332 A | 1/1980 | Delaney |
| 4,254,771 A | 3/1981 | Vidal |
| 4,319,571 A | 3/1982 | Winchell |
| 4,333,460 A | 6/1982 | Miller |
| 4,344,434 A | 8/1982 | Robertson |
| 4,403,991 A | 9/1983 | Hill |
| 4,406,655 A | 9/1983 | Clayton |
| 4,419,099 A | 12/1983 | Miller |
| 4,443,219 A | 4/1984 | Meisch et al. |
| 4,493,711 A | 1/1985 | Chin et al. |
| 4,496,356 A | 1/1985 | Lognion |
| 4,504,270 A | 3/1985 | Miller |
| 4,516,578 A | 5/1985 | Shuffield |
| 4,581,763 A | 4/1986 | Olsen |
| 4,596,554 A | 6/1986 | Dastgeer |
| 4,637,814 A | 1/1987 | Leiboff |
| 4,664,114 A | 5/1987 | Ghodsian |
| 4,717,388 A | 1/1988 | Steer et al. |
| 4,721,508 A | 1/1988 | Burton |
| 4,752,288 A | 6/1988 | Hussey |
| 4,762,128 A | 8/1988 | Rosenbluth |
| 4,772,260 A | 9/1988 | Heyden |
| 4,786,283 A | 11/1988 | Andersson et al. |
| 4,804,375 A | 2/1989 | Robertson |
| 4,820,270 A | 4/1989 | Hardcastle et al. |
| 4,823,812 A | 4/1989 | Eshel et al. |
| 4,850,986 A | 7/1989 | Temple |
| 4,949,756 A | 8/1990 | Melinyshyn et al. |
| 4,986,822 A | 1/1991 | Anderson |
| 5,019,056 A | 5/1991 | Lee et al. |
| 5,041,100 A | 8/1991 | Rowland et al. |
| 5,045,070 A | 9/1991 | Grodecki et al. |
| 5,074,842 A | 12/1991 | Clayton |
| 5,100,626 A | 3/1992 | Levin |
| 5,108,369 A | 4/1992 | Ganguly et al. |
| 5,171,305 A | 12/1992 | Schickling et al. |
| 5,176,630 A | 1/1993 | Shilling et al. |
| 5,197,950 A | 3/1993 | Clayton |
| 5,213,576 A | 5/1993 | Abiuso et al. |
| 5,217,439 A | 6/1993 | McClusky |
| 5,269,755 A | 12/1993 | Bodicky |
| 5,284,480 A | 2/1994 | Porter et al. |
| 5,286,259 A | 2/1994 | Ganguly et al. |
| 5,295,979 A | 3/1994 | DeLaurentis et al. |
| 5,306,226 A | 4/1994 | Salama |
| 5,336,252 A | 8/1994 | Cohen |
| 5,354,220 A | 10/1994 | Ganguly et al. |
| 5,355,872 A | 10/1994 | Riggs et al. |
| 5,356,400 A | 10/1994 | Temple |
| 5,370,624 A | 12/1994 | Edwards et al. |
| 5,395,331 A | 3/1995 | O'Neill et al. |
| 5,399,164 A | 3/1995 | Snoke et al. |
| 5,405,319 A | 4/1995 | Abell et al. |
| 5,421,827 A | 6/1995 | Temple |
| 5,425,710 A | 6/1995 | Khair et al. |
| 5,520,669 A | 5/1996 | Mulholland |
| 5,536,234 A | 7/1996 | Newman |
| 5,569,216 A | 10/1996 | Kim |
| 5,569,219 A | 10/1996 | Hakki et al. |
| 5,609,583 A | 3/1997 | Hakki et al. |
| 5,624,397 A | 4/1997 | Snoke et al. |
| 5,637,091 A | 6/1997 | Hakky et al. |
| 5,660,205 A | 8/1997 | Epstein |
| 5,707,362 A | 1/1998 | Yoon |
| 5,716,321 A | 2/1998 | Kerin et al. |
| 5,741,239 A | 4/1998 | Mulholland |
| 5,762,996 A | 6/1998 | Lucas et al. |
| 5,797,147 A | 8/1998 | Young et al. |
| 5,855,549 A | 1/1999 | Newman |
| 5,935,056 A | 8/1999 | Kerin et al. |
| 5,935,098 A | 8/1999 | Blaisdell et al. |
| 5,941,860 A | 8/1999 | Wheeler |
| 5,997,517 A | 12/1999 | Whitbourne |
| 5,997,546 A | 12/1999 | Foster et al. |
| 6,007,521 A | 12/1999 | Bidwell et al. |
| 6,033,390 A | 3/2000 | von Dyck |
| 6,050,934 A | 4/2000 | Mikhail et al. |
| 6,096,057 A | 8/2000 | Klingenstein |
| 6,106,506 A | 8/2000 | Abell et al. |
| 6,132,399 A | 10/2000 | Shultz |
| 6,159,195 A | 12/2000 | Ha et al. |
| 6,194,659 B1 | 2/2001 | Cornu et al. |
| 6,340,465 B1 | 1/2002 | Hsu et al. |
| 6,342,052 B1 | 1/2002 | Allende |
| 6,350,255 B1 | 2/2002 | von Dyck |
| 6,364,858 B1 | 4/2002 | Picha |
| 6,413,228 B1 | 7/2002 | Hung et al. |
| 6,419,664 B1 | 7/2002 | von Bulow et al. |
| 6,485,476 B1 | 11/2002 | von Dyck et al. |
| 6,508,794 B1 | 1/2003 | Palumbo et al. |
| 6,527,755 B1 | 3/2003 | Salama |
| 6,569,132 B1 | 5/2003 | Dvarsater |
| 6,575,932 B1 | 6/2003 | O'Brien et al. |
| 6,576,429 B1 | 6/2003 | Hallgren et al. |
| 6,579,539 B2 | 6/2003 | Lawson et al. |
| 6,595,971 B1 | 7/2003 | von Dyck et al. |
| 6,596,401 B1 | 7/2003 | Terry et al. |
| 6,629,955 B2 | 10/2003 | Morris et al. |
| 6,652,508 B2 | 11/2003 | Griffin et al. |
| 6,716,209 B2 | 4/2004 | Leiboff |
| 6,716,252 B2 | 4/2004 | Lazarovitz et al. |
| 6,716,895 B1 | 4/2004 | Terry |
| 6,719,709 B2 | 4/2004 | Whalen et al. |
| 6,758,857 B2 | 7/2004 | Cioanta et al. |
| 6,802,808 B2 | 10/2004 | Brady |
| 6,843,766 B1 | 1/2005 | Nemir et al. |
| 6,939,332 B2 | 9/2005 | Perlo et al. |
| 6,949,598 B2 | 9/2005 | Terry |
| 6,968,577 B1 | 11/2005 | Taft, Jr. |
| 6,981,155 B1 | 12/2005 | Lyle et al. |
| 7,021,466 B2 | 4/2006 | Kuske et al. |
| 7,025,716 B1 | 4/2006 | Meloul et al. |
| 7,066,917 B2 | 6/2006 | Talamonti |
| 7,077,841 B2 | 7/2006 | Gaiser et al. |
| 7,095,716 B1 | 8/2006 | Ke et al. |
| 7,147,627 B2 | 12/2006 | Kim et al. |
| 7,179,849 B2 | 2/2007 | Terry |
| 7,223,260 B2 | 5/2007 | Hansen et al. |
| 7,297,132 B2 | 11/2007 | Perlo et al. |
| 7,338,478 B2 | 3/2008 | Leiboff |
| 7,722,583 B2 | 5/2010 | Kim et al. |
| 7,727,188 B2 | 6/2010 | Machado et al. |
| 7,862,541 B2 | 1/2011 | Jeffrey et al. |
| 7,947,025 B2 | 5/2011 | Buglino et al. |
| 8,016,816 B2 | 9/2011 | Gregory |
| 8,057,448 B2 | 11/2011 | Williams et al. |

(56) References Cited

U.S. PATENT DOCUMENTS

| | | | |
|---|---|---|---|
| 8,070,736 B2 | 12/2011 | Nishtala et al. |
| 8,070,737 B2 | 12/2011 | Cline et al. |
| 8,075,539 B2 | 12/2011 | Nishtala et al. |
| 8,075,540 B2 | 12/2011 | von Dyck et al. |
| 8,092,437 B2 | 1/2012 | Cline |
| 8,096,980 B2 | 1/2012 | Cline |
| 8,323,255 B2 | 12/2012 | Martino et al. |
| 8,388,586 B2 | 3/2013 | Weig |
| 8,597,266 B2 | 12/2013 | Nishtala et al. |
| 8,777,912 B2 | 7/2014 | Nishtala et al. |
| 8,926,577 B2 | 1/2015 | Nishtala et al. |
| 9,456,920 B2 | 10/2016 | Nishtala et al. |
| 9,463,110 B2 | 10/2016 | Nishtala et al. |
| 2001/0044595 A1 | 11/2001 | Reydel et al. |
| 2002/0016607 A1 | 2/2002 | Bonadio et al. |
| 2002/0019613 A1 | 2/2002 | Alexandersen |
| 2002/0072789 A1 | 6/2002 | Hackett et al. |
| 2002/0077611 A1 | 6/2002 | von Dyck et al. |
| 2002/0138052 A1 | 9/2002 | Perlo et al. |
| 2002/0151871 A1 | 10/2002 | Gaiser et al. |
| 2002/0165521 A1 | 11/2002 | Cioanta et al. |
| 2003/0023204 A1 | 1/2003 | Vo et al. |
| 2003/0036682 A1 | 2/2003 | Leber et al. |
| 2003/0040727 A1 | 2/2003 | Boulanger et al. |
| 2003/0100886 A1 | 5/2003 | Segal et al. |
| 2003/0130646 A1 | 7/2003 | Kubalak et al. |
| 2003/0195478 A1 | 10/2003 | Russo |
| 2003/0220621 A1 | 11/2003 | Arkinstall |
| 2004/0006305 A1 | 1/2004 | Hebert et al. |
| 2004/0034333 A1 | 2/2004 | Seese et al. |
| 2004/0039348 A1 | 2/2004 | Kim et al. |
| 2004/0068243 A1 | 4/2004 | Hansen et al. |
| 2004/0082859 A1 | 4/2004 | Schaer |
| 2004/0116830 A1 | 6/2004 | Trudeau et al. |
| 2004/0236293 A1 | 11/2004 | Tanghoj et al. |
| 2004/0256004 A1 | 12/2004 | Kessell et al. |
| 2005/0004533 A1 | 1/2005 | Smith |
| 2005/0033226 A1 | 2/2005 | Kim |
| 2005/0038380 A1 | 2/2005 | Nemir et al. |
| 2005/0054996 A1 | 3/2005 | Gregory |
| 2005/0055080 A1 | 3/2005 | Istephanous et al. |
| 2005/0097350 A1 | 5/2005 | Patrick et al. |
| 2005/0125002 A1 | 6/2005 | Baran et al. |
| 2005/0137526 A1 | 6/2005 | Machado et al. |
| 2005/0148954 A1 | 7/2005 | Abell |
| 2005/0228363 A1 | 10/2005 | Leiboff |
| 2005/0256464 A1 | 11/2005 | Pallas |
| 2005/0256465 A1 | 11/2005 | Perlo et al. |
| 2005/0271694 A1 | 12/2005 | Mansouri et al. |
| 2006/0009732 A1 | 1/2006 | Hardy |
| 2006/0025728 A1 | 2/2006 | Leiboff et al. |
| 2006/0052759 A1 | 3/2006 | Johansson et al. |
| 2006/0069300 A1 | 3/2006 | Levien |
| 2006/0100595 A1 | 5/2006 | von Dyck et al. |
| 2006/0149129 A1 | 7/2006 | Watts et al. |
| 2006/0189951 A1 | 8/2006 | Kim et al. |
| 2006/0195006 A1 | 8/2006 | Daurelle et al. |
| 2006/0271087 A1 | 11/2006 | Von Dyck et al. |
| 2006/0276746 A1* | 12/2006 | Burnside et al. ............. 604/103 |
| 2007/0049878 A1 | 3/2007 | Kim et al. |
| 2007/0066965 A1 | 3/2007 | Coambs et al. |
| 2007/0073216 A1 | 3/2007 | McAuliffe et al. |
| 2007/0149922 A1 | 6/2007 | Schneider et al. |
| 2007/0265617 A1 | 11/2007 | Falkenstein et al. |
| 2008/0004568 A1 | 1/2008 | Jeffrey et al. |
| 2008/0096189 A1 | 4/2008 | Boone et al. |
| 2008/0097270 A1 | 4/2008 | Utterberg et al. |
| 2008/0183202 A1 | 7/2008 | Isham |
| 2008/0262447 A2 | 10/2008 | Martino et al. |
| 2009/0030386 A1 | 1/2009 | Kim et al. |
| 2009/0030387 A1 | 1/2009 | Kim et al. |
| 2009/0082743 A1 | 3/2009 | Buglino et al. |
| 2009/0227970 A1 | 9/2009 | Nishtala et al. |
| 2009/0227971 A1 | 9/2009 | Nishtala et al. |
| 2009/0247969 A1 | 10/2009 | Nishtala et al. |
| 2010/0280489 A1 | 11/2010 | Nishtala et al. |
| 2010/0298739 A1 | 11/2010 | Steube et al. |
| 2011/0160657 A1 | 6/2011 | Gobel |
| 2011/0218508 A1 | 9/2011 | Cason |
| 2011/0282311 A1 | 11/2011 | Nishtala |
| 2011/0313378 A1 | 12/2011 | Gregory |
| 2013/0110087 A1 | 5/2013 | Kane |
| 2013/0218108 A1 | 8/2013 | Nishtala et al. |
| 2014/0094760 A1 | 4/2014 | Nishtala et al. |
| 2014/0323990 A1 | 10/2014 | Nishtala et al. |
| 2017/0020711 A1 | 1/2017 | Nishtala et al. |

FOREIGN PATENT DOCUMENTS

| | | |
|---|---|---|
| EP | 1514572 A2 | 3/2005 |
| EP | 1749507 A2 | 2/2007 |
| EP | 1819295 A1 | 8/2007 |
| EP | 1900390 A2 | 3/2008 |
| EP | 2027832 A2 | 2/2009 |
| EP | 2044966 A2 | 4/2009 |
| EP | 2047874 A1 | 4/2009 |
| EP | 2073861 A2 | 7/2009 |
| EP | 2349375 A1 | 8/2011 |
| EP | 2364679 A1 | 9/2011 |
| EP | 2399554 A1 | 12/2011 |
| EP | 2404630 A2 | 1/2012 |
| GB | 1379772 A | 1/1975 |
| JP | 09-094296 A | 4/1997 |
| JP | 2005533618 A | 11/2005 |
| JP | 2008-183440 A | 8/2008 |
| JP | 2012509110 A | 4/2012 |
| KR | 109896 | 4/1997 |
| KR | 118334 | 4/1998 |
| WO | 9108013 A1 | 6/1991 |
| WO | 9743987 A1 | 11/1997 |
| WO | 9930652 A1 | 6/1999 |
| WO | WO-0197740 | 12/2001 |
| WO | 03/035147 A1 | 5/2003 |
| WO | 03086507 A1 | 10/2003 |
| WO | 2004018022 A1 | 3/2004 |
| WO | WO-2005016136 A1 | 2/2005 |
| WO | WO-2006004943 | 1/2006 |
| WO | 2006052627 A1 | 5/2006 |
| WO | 2006058286 A2 | 6/2006 |
| WO | WO-2006062912 | 6/2006 |
| WO | 2007076483 A1 | 7/2007 |
| WO | 2008103788 A1 | 8/2008 |
| WO | 2008103789 A2 | 8/2008 |
| WO | 2008134334 A1 | 11/2008 |
| WO | 2008157172 A1 | 12/2008 |
| WO | 2009015152 A1 | 1/2009 |
| WO | 2009029610 A1 | 3/2009 |
| WO | 2009135141 A1 | 11/2009 |
| WO | 2009155537 A1 | 12/2009 |
| WO | 2010057208 A1 | 5/2010 |
| WO | 2011031822 A1 | 3/2011 |
| WO | 2011100187 A1 | 8/2011 |
| WO | 2012058388 A1 | 5/2012 |

OTHER PUBLICATIONS

Sep. 26, 2009 International Search Report in international application No. PCT/US2008/070781 filed on Jul. 22, 2008.

Sep. 16, 2008 Written Opinion of the ISA in international application No. PCT/US2008/70781 filed on Jul. 22, 2008.

Jan. 26, 2010 International Preliminary Report on Patentability in international application No. PCT/US2008/070781 filed on Jul. 22, 2007.

Feb. 10, 2009 International Search Report in international application No. PCT/US2008/081120 filed on Oct. 11, 2007.

Beahrs et al. "Indwelling Ileostomy Valve Device" Am J Surg. 141 (1): 111-115 (Jan. 1981).

Bosley "Three Methods of Stool Management for Patients with Diarrhea," Ostomy/Wound Management, vol. 40, No. 1, pp. 52-57 (Jan./Feb. 1994).

Echols et al "Initial Experience With a New System for the Control and Containment of Fecal Output for the Protection of Patients in a

(56) References Cited

OTHER PUBLICATIONS

Large Burn Center," Abstract of Oral Presentation John A. Boswich, MD Burn and Wound Care Symposium (Feb. 2004, Augusta, GA).
Echols et al "Initial Experience With a New System for the Control and Containment of Fecal Output in Burn Patients," Doctors Hospital Joseph M. Still Burn Center (undated).
Grillo "A Low-Pressure Cuff for Endotracheal Tubes to Minimize Tracheal Injury" Jour. Thorac. & Card. Surg., vol. 62, No. 6, pp. 898-907 (Dec. 1971).
Kim et al. "Clinical Application of Continent Anal Plug in Bed-Ridden Patient with Intractable Diarrhea," Poster at American Society of Colon and Rectal Surgeons (Jun. 25-29, 2000, Boston, MA).
Kim et al. "Clinical Application of Continent Anal Plug in Bed-Ridden Patients with Intractable Diarrhea" Annual Meeting of the ASCRS (Jun. 24-29, 2000, Boston, MA).
Kim et al., "Clinical Application of Continent Anal Plug in Bed-Ridden Patient with Intractable Diarrhea" (with translation), Jnl. of the Korean Soc'y of Coloproctology, vol. 16, No. 3 (2000).
Kim, et al. "Clinical Application of Continent Anal Plug in Bed-Ridden Patients with Intractable Diarrhea," Dis. Colon Rectum, vol. 44, No. 8, pp. 1162-1167 (Aug. 2001).
Kim, et al., "Passive Bowel Movement Effects Using a New Colostomy Device: An Acute Experiment on a Dog" (with translation), Jnl. of the Korean Soc'y of Coloproctology, vol. 14, No. 3 (1998).
Leventon "New Coatings and Processes Add Value to Medical Devices," Medical Device & Diagnostic Industry (Aug. 2001).
Lim et al. "Application of a New Colostomy Device in Incontinent Dog Model," Journal of Korean Society of Coloproctology (Sep. 1998).
Lim et al., "Application of a New Colostomy Device in Incontinent Dog Model" (with translation), Jnl. of the Korean Soc'y of Coloproctology, vol. 14, No. 3 (presented at the 16th conference of the ISUCRS, held in Malmo, Sweden in 1998).
Nelson et al. "Fecal Incontinence in Wisconsin Nursing Homes: Prevalence and Associations," Diseases of the Colon & Rectum, vol. 41(10), pp. 1226-1229 (http://gateway1.ovid.com/ovidweb.cgi) (Oct. 1998).
Numanoglu "Colostomy Control Device," Artifical Organs 10(1):63-65 (Feb. 1986).
PCT/US2007/081120 filed Oct. 11, 2007 Preliminary Report on Patentability dated Apr. 22, 2009.
PCT/US2007/081120 filed Oct. 11, 2007 Written Opinion dated May 1, 2008.
PCT/US2009/064846 filed Nov. 17, 2009 Search Report dated Jan. 20, 2010.
PCT/US2009/064846 filed Nov. 17, 2009 Written Opinion dated Jan. 20, 2010.
Pemberton et al. "A continent Ileostomy Device," Annals of Surgery 197(5):618-626 (May 1983).
Scammell et al. "Influence of Rectal Washout on Bacterial Counts in the Rectal Stump," British Journal of Surgery, vol. 72 (Jul. 1985).
U.S. Appl. No. 12/463,342, filed May 8, 2009 Non-Final Office Action dated Jan. 31, 2011.
U.S. Appl. No. 12/475,346, filed May 29, 2009 Non-Final Office Action dated Feb. 11, 2011.
Wolf "Comparing Liquid and High Consistency Silicone Rubber Elastomers: Which is Right for You?" Medical Plastics and Biomaterials, vol. 4, No. 4 (Jul./Aug. 1997).
Wolgemuth "Assessing the Performance and Suitability of Parylene Coating," Medical Device & Diagnostic Industry (Aug. 2000).
Zassi Medical Evolutions "Bowel Management System Quick Reference Guide" (2003).
Zassi Medical Evolutions "Bowel Management System Quick Reference Guide" P/N 300-75/0003 (undated).
Zassi Medical Evolutions Product Brochure "Bowel Management System Instructions for Use" P/N 300-75-0001, Rev E (Jun. 2004).
Zassi Medical Evolutions website "The Bowel Management System (BMS) Benefits" (2005).
Zassi Medical Evolutions website "The Bowel Management System (BMS) FAQ: The Product" (2005).
Zassi Medical Evolutions website "The Bowel Management System (BMS)" (2005).
CN 200780038926.8 filed Oct. 11, 2007 Notice to Grant dated Oct. 10, 2012.
CN 200780038926.8 filed Oct. 11, 2007 Office Action dated Jun. 29, 2012.
U.S. Appl. No. 12/438,200, filed Feb. 20, 2009 Final Office Action dated Dec. 29, 2011.
U.S. Appl. No. 12/438,200, filed Feb. 20, 2009 Advisory Action dated Mar. 13, 2012.
U.S. Appl. No. 12/467,232, filed May 15, 2009 Advisory Action dated Jul. 5, 2013.
U.S. Appl. No. 12/467,232, filed May 15, 2009 Final Office Action dated Apr. 24, 2013.
U.S. Appl. No. 12/467,232, filed May 15, 2009 Non-Final Office Action dated Nov. 21, 2012.
U.S. Appl. No. 12/467,232, filed May 15, 2009 Notice of Allowance dated Aug. 9, 2013.
U.S. Appl. No. 12/669,876, filed Jun. 18, 2010 Advisory Action dated Apr. 12, 2013.
U.S. Appl. No. 12/669,876, filed Jun. 18, 2010 Final Office Action dated Jan. 23, 2013.
U.S. Appl. No. 12/669,876, filed Jun. 18, 2010 Non-Final Office Action dated Jun. 6, 2012.
U.S. Appl. No. 12/669,876, filed Jun. 18, 2010 Non-Final Office Action dated Nov. 8, 2013.
U.S. Appl. No. 13/129,767, filed Jul. 29, 2011 Advisory Action dated May 10, 2013.
U.S. Appl. No. 13/129,767, filed Jul. 29, 2011 Final Office Action dated Feb. 8, 2013.
U.S. Appl. No. 13/129,767, filed Jul. 29, 2011 Non-Final Office Action dated Sep. 12, 2012.
CN 200780038926 filed Oct. 11, 2007 Office Action dated Jun. 21, 2011.
CN 200780038926.8 filed Oct. 11, 2007 Office Action dated Mar. 12, 2012.
PCT/US2009/064846 filed Nov. 17, 2009 Preliminary Report on Patentability dated May 26, 2011.
U.S. Appl. No. 12/438,200, filed Feb. 20, 2009 Non-Final Office Action dated Jun. 23, 2011.
U.S. Appl. No. 12/463,342, filed May 8, 2009 Notice of Allowance dated Jul. 27, 2011.
U.S. Appl. No. 12/475,346, filed May 29, 2009 Notice of Allowance dated Jul. 29, 2011.
CA 2666631 Second Examiner's Report dated May 2, 2014.
U.S. Appl. No. 13/129,767, filed Jul. 29, 2011 Non-Final Office Action dated Jun. 12, 2014.
CA 2,743,167 filed Nov. 17, 2009 Examiner's Report dated Aug. 18, 2016.
CA 2,743,167 filed Nov. 17, 2009 First Examiner's Report dated Dec. 4, 2015.
CA 2,916,746 filed Jan. 6, 2016 Examiner's Report dated Jan. 20, 2017.
CA 2666631 Third Examiner's Report dated Nov. 25, 2014.
U.S. Appl. No. 12/438,200, filed Feb. 20, 2009 Notice of Allowance dated Sep. 2, 2014.
U.S. Appl. No. 13/129,767, filed Jul. 29, 2011 Final Office Action dated Dec. 18, 2014.
U.S. Appl. No. 13/129,767, filed Jul. 29, 2011 Final Office Action dated May 19, 2016.
U.S. Appl. No. 13/129,767, filed Jul. 29, 2011 Non-Final Office Action dated Oct. 29, 2015.
U.S. Appl. No. 13/852,925, filed Mar. 28, 2013 Non-Final Office Action dated Dec. 9, 2015.
U.S. Appl. No. 13/852,925, filed Mar. 28, 2013 Notice of Allowance dated May 10, 2016.
U.S. Appl. No. 14/032,954, filed Sep. 20, 2013 Non-Final Office Action dated Dec. 14, 2015.
U.S. Appl. No. 14/032,954, filed Sep. 20, 2013 Notice of Allowance dated May 23, 2016.

(56) References Cited

OTHER PUBLICATIONS

U.S. Appl. No. 14/328,264, filed Jul. 10, 2014 Final Office Action dated Feb. 9, 2017.
U.S. Appl. No. 14/328,264, filed Jul. 10, 2014 Non-Final Office Action dated Sep. 13, 2016.
CA 2,743,167 filed Nov. 17, 2009 Examiner's Report dated Apr. 7, 2017.
EP 09826988.9 filed May 25, 2011 Extended European Search Report dated Apr. 4, 2017.

* cited by examiner

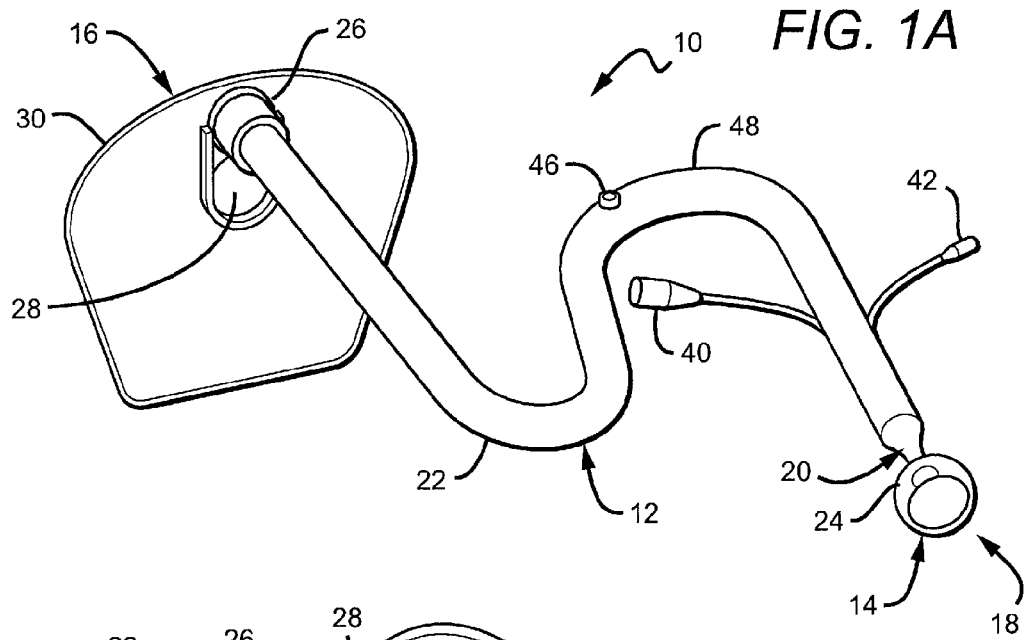
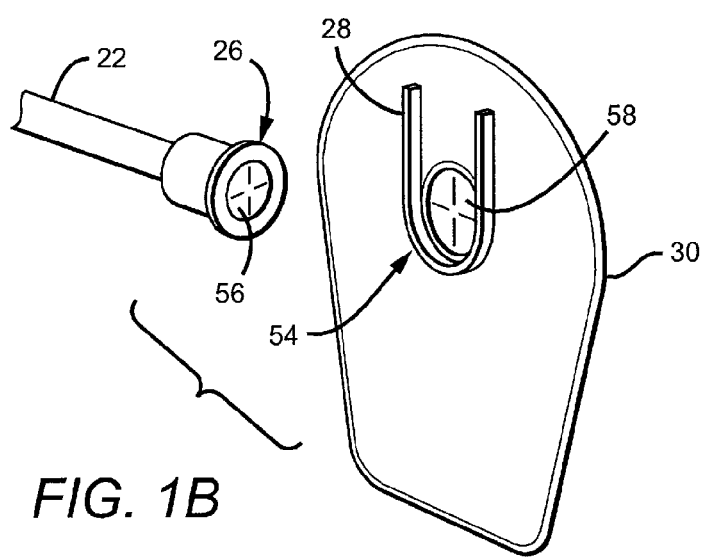
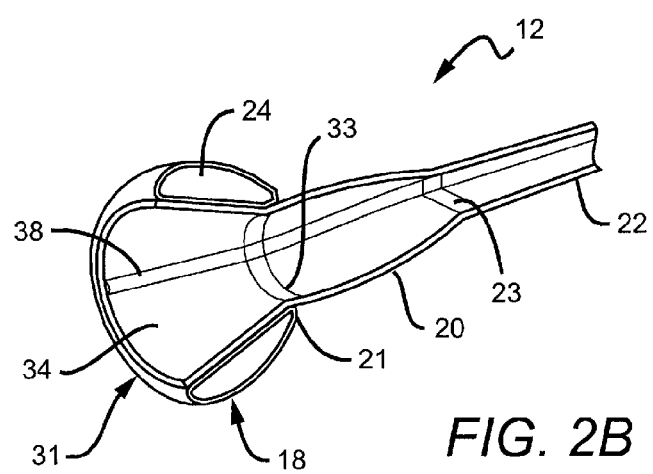

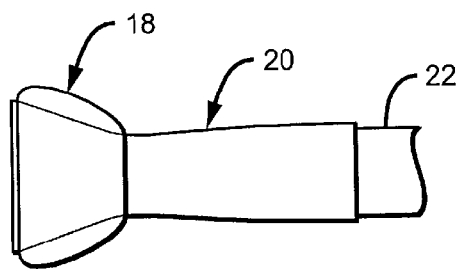
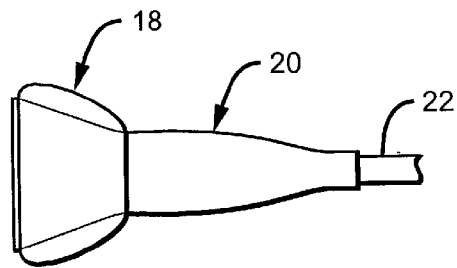
FIG. 2G    FIG. 2H
FIG. 2I
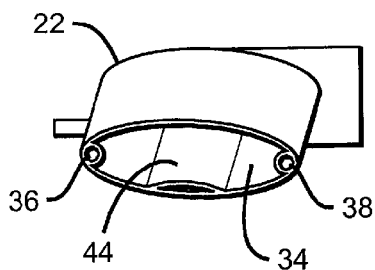
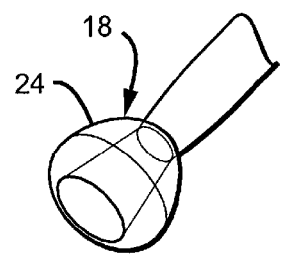
FIG. 3A
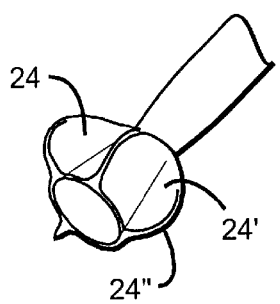
FIG. 3B
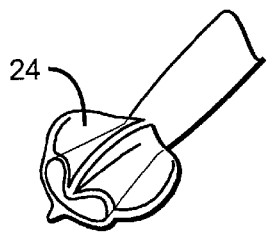
FIG. 3C
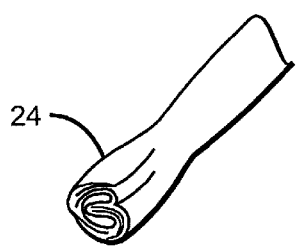
FIG. 3D FIG. 6
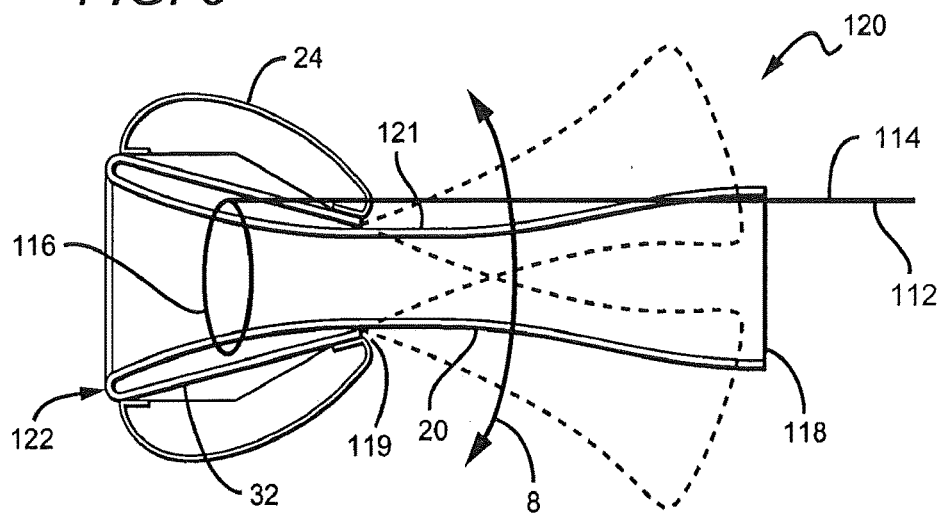
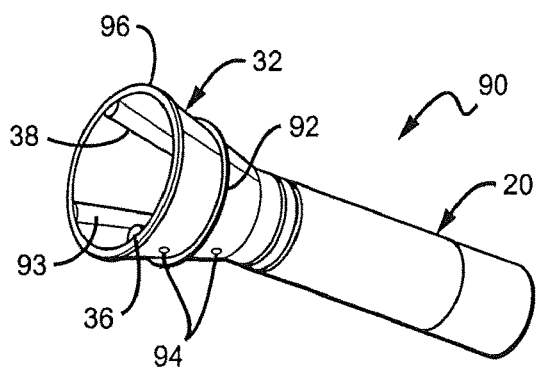
FIG. 7A
FIG. 7B
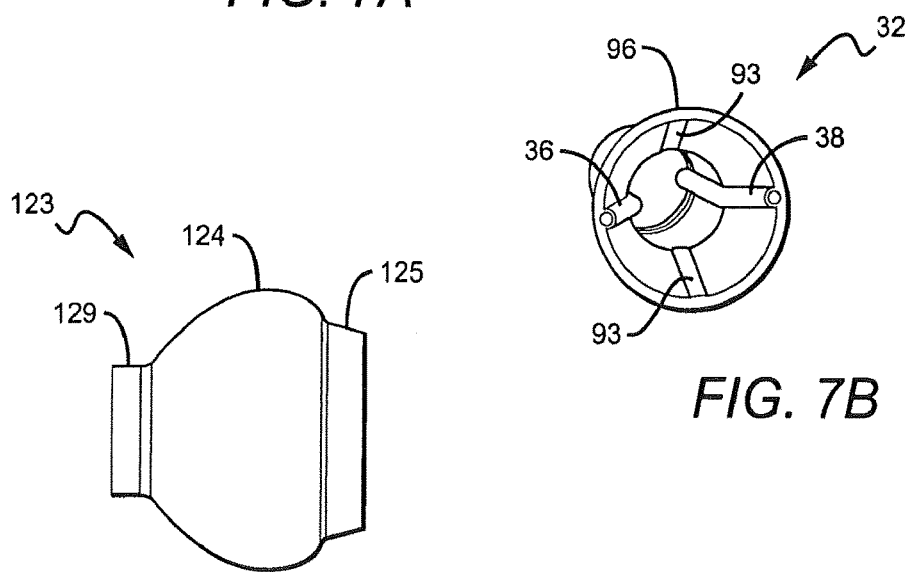
FIG. 7C

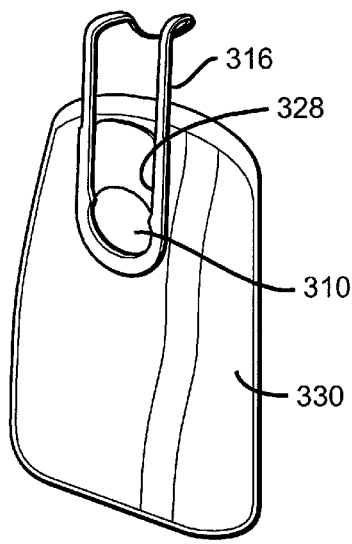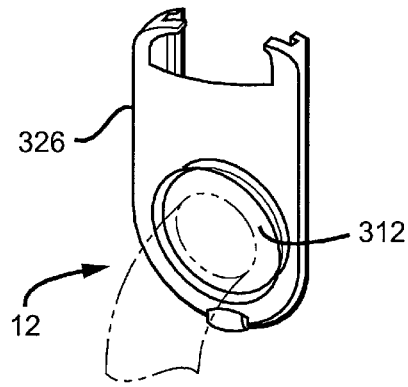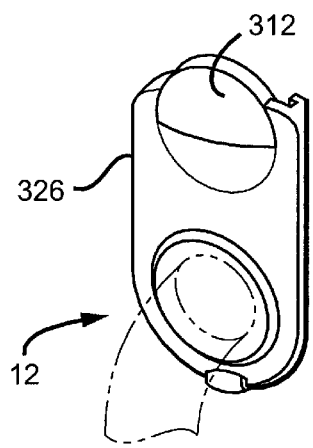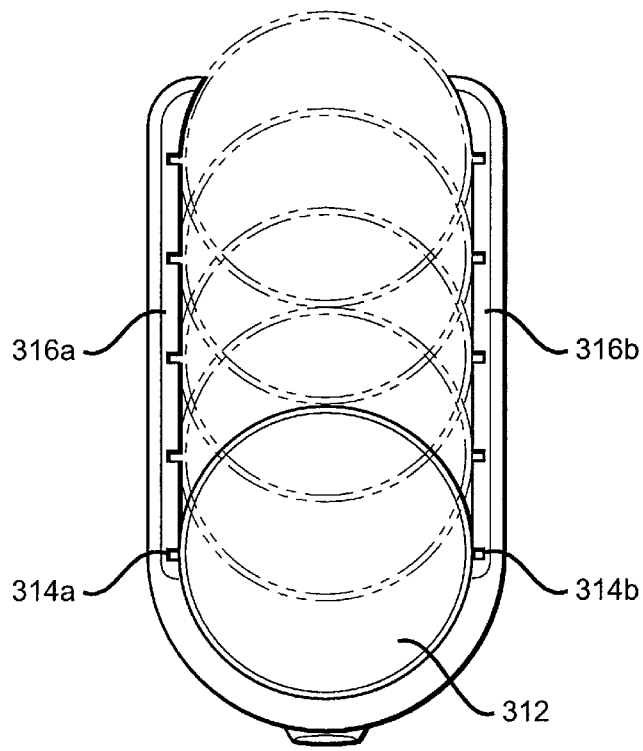
FIG. 11A
FIG. 11B
FIG. 11C
FIG. 11D

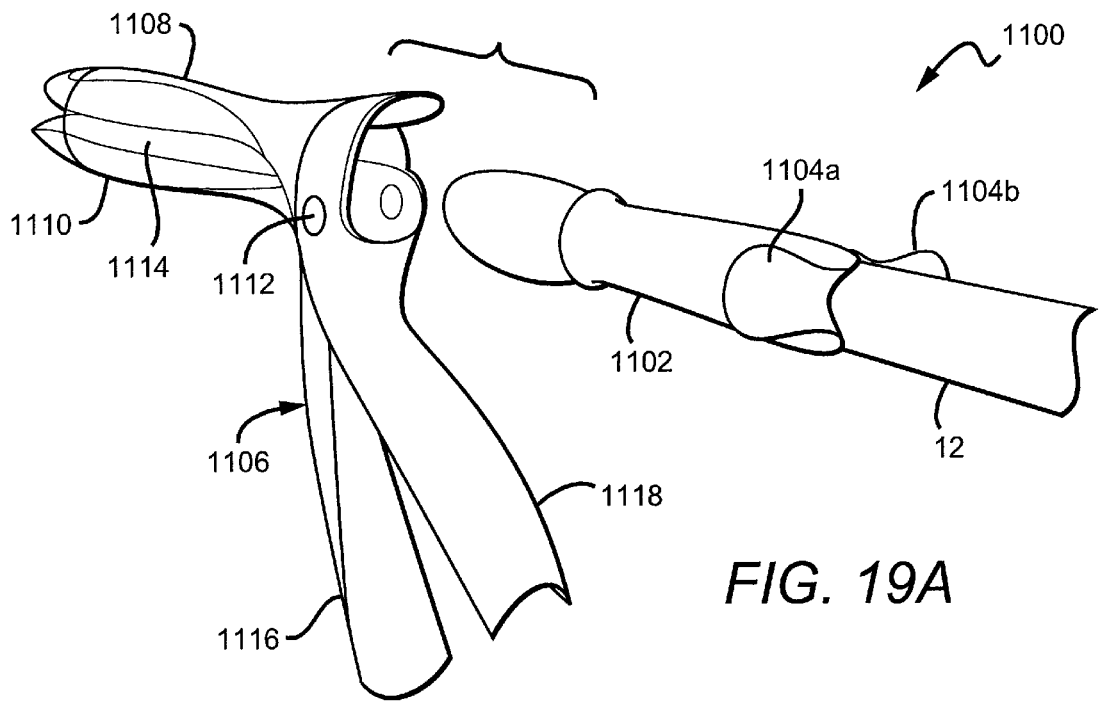
FIG. 19A
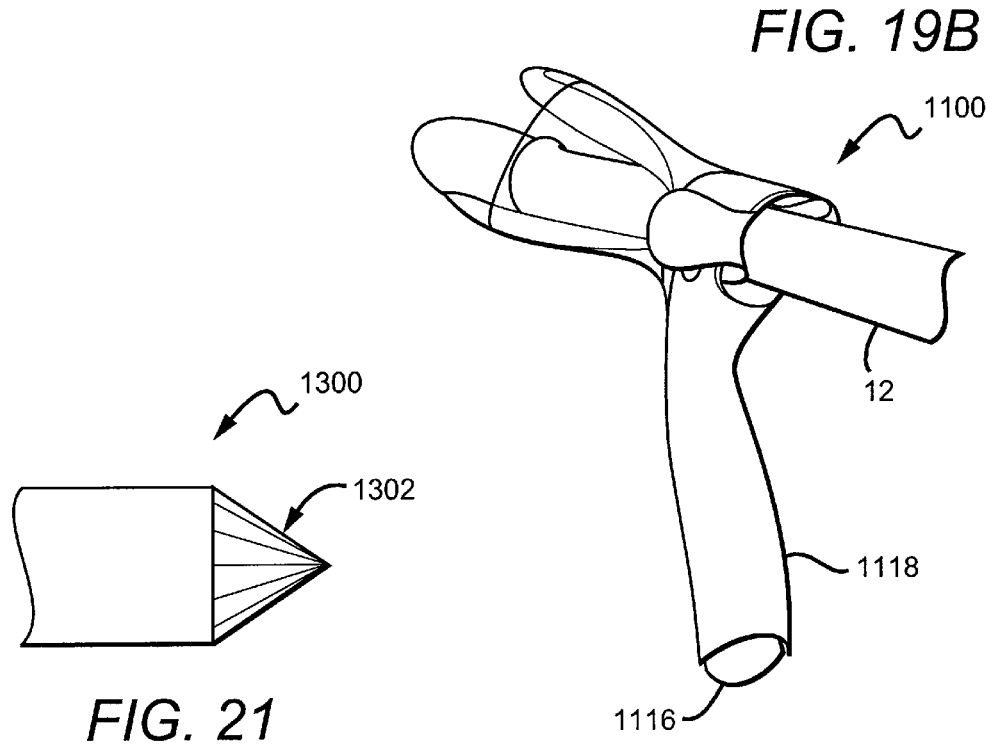
FIG. 19B
FIG. 21

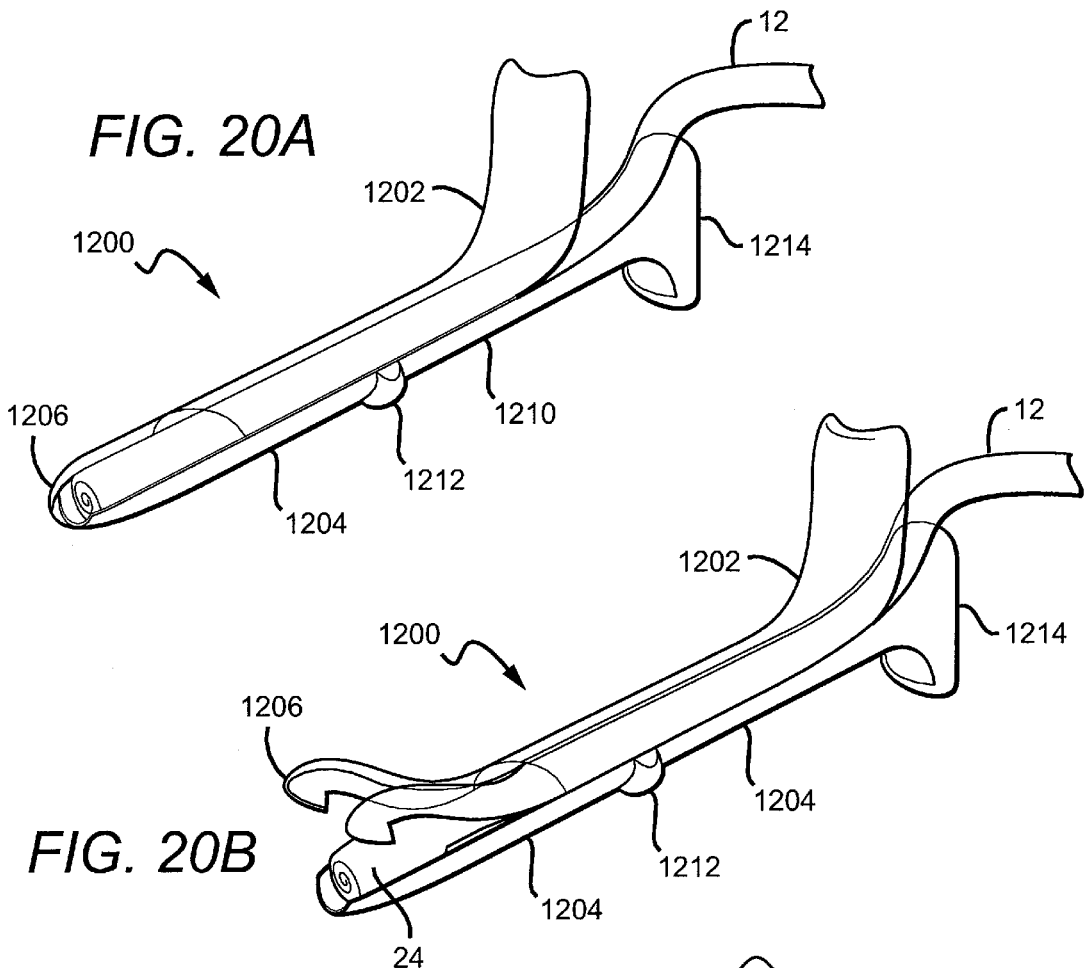
FIG. 20A
FIG. 20B
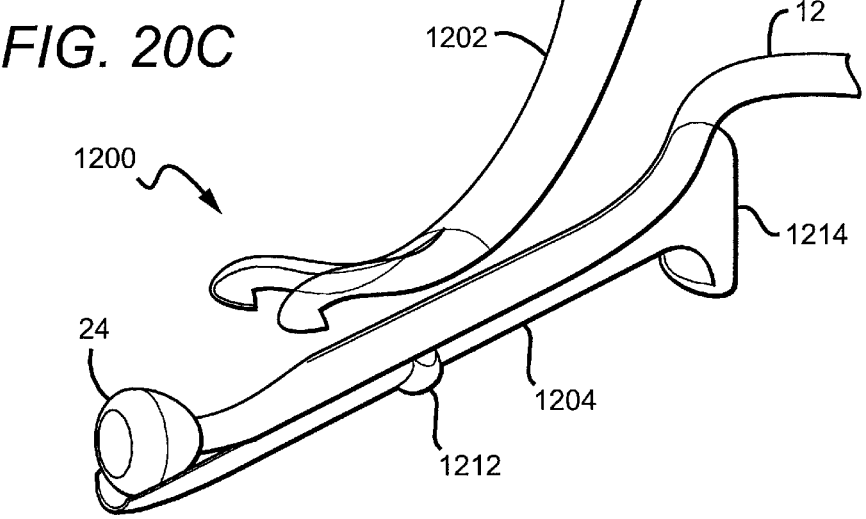
FIG. 20C

WASTE MANAGEMENT SYSTEM

PRIORITY

This application is a divisional of U.S. patent application Ser. No. 12/438,200, filed Feb. 20, 2009, now U.S. Pat. No. 8,926,577, which is a U.S. national stage application under 35 USC §371 of International Application No. PCT/US2007/081120, filed Oct. 11, 2007, which claims the benefit of priority to U.S. Provisional Patent Application No. 60/958,217, filed Jul. 3, 2007, and to U.S. Provisional Patent Application No. 60/829,758, filed Oct. 17, 2006, each of which applications is incorporated by reference into this application as if fully set forth herein.

BACKGROUND

Waste management systems are important in the healthcare field, particularly for patients that are unable to care for themselves. Such patients may suffer from incontinent diarrhea or like maladies and, due to their condition (e.g., severe burns, surgical incisions, etc.), may be susceptible to infections should the fecal matter come in contact with an open wound, burn, surgical site, etc. Moreover, healthcare professionals that come in contact with the fecal matter while attending to the patient may be susceptible to disease and/or the spreading thereof. Thus, a suitable waste management system, at minimum, substantially contains fecal matter within a closed system so as to avoid, for example, substantial skin breakdown, infection risk, cross-contamination of pathogens, problematic patient clean-up, patient discomfort, etc. While fecal management systems are described in the art, many known issues remain unsolved or unaddressed.

The following references relate to fecal management systems or components thereof: U.S. Pat. No. 5,569,216 to Kim; U.S. Pat. No. 6,527,755 to Salama; U.S. Pat. No. 7,147,627 to Kim et al.; U.S. Patent Application Publication No. 2005/0054996 to Gregory; U.S. Patent Application Publication No. 2005/0137526 to Machado et al.; U.S. Patent Application Publication No. 2006/0189951 to Kim et al.; U.S. Patent Application Publication No. 2006/0271087 to Von Dyck et al.; U.S. Patent Application Publication No. 2007/0049878 to Kim et al.; and U.S. Patent Application Publication No. 2007/0149922 to Schneider et al., each of which is incorporated by reference in its entirety into this application.

Applicants have recognized that it would be desirable to provide a waste management system that is robust, comfortable for the patient, eliminates known issues and has features that facilitate its use, embodiments of which are described herein.

BRIEF SUMMARY

Accordingly, a waste management system is described herein, the system including a waste transport device and a waste collection device. The waste transport device may include a first connector member configured for releasable connection to a second connector member on the waste collection device. The system may also include an insertion device to facilitate insertion of the waste transport device into the rectum of a patient.

In one embodiment, a waste management system includes a waste transport device, including a collection member with a distal end opening having a first cross-sectional area and a proximal end opening having a second cross-sectional area less than the first cross-sectional area, a retention cuff disposed about an outer surface of the collection member, and a waste collection device.

In another embodiment, a waste transport device includes a distal section defining a distal end opening having a first cross-sectional area and a proximal end opening having a second cross-sectional area less than the first cross-sectional area, the distal section including an inflatable retention cuff, a proximal section including a flush lumen, a connector coupled to a proximal end of the proximal section, and an intermediate section connecting the proximal section to the distal section, the intermediate section including a transitioning cross-sectional shape from a proximal end to a distal end. In another embodiment, a waste transport device includes a collection member including a lumen connecting a distal end opening to a proximal end opening and a retention cuff disposed about an outer surface of the collection member, the retention cuff including a pain relief drug.

In one embodiment, a method of managing the fecal material of a patient, includes inserting a distal section of a waste transport system in a collapsed configuration into a patient's rectum, the distal section in an expanded configuration defining a distal end opening having a first cross-sectional area and a proximal end opening having a second cross-sectional area less than the first cross-sectional area, the distal section including an inflatable retention cuff, removing the insertion device from the waste transport system, and inflating the retention cuff to a first inflated configuration.

In another embodiment, a method of connecting a waste transport device to a waste collection device includes associating a first connector coupled to the waste transport device with a second connector coupled to the waste collection device by aligning an aperture of the first connector with an aperture of the second connector and pressing an end of one or more locking arms of the first connector into slots of the second connector, and sliding the first and second connectors to align the apertures with a central lumen of the waste transport device and an opening of the waste collection device.

These and other embodiments, features and advantages will become more apparent to those skilled in the art when taken with reference to the following more detailed description in conjunction with the accompanying drawings that are first briefly described.

BRIEF DESCRIPTION OF THE DRAWINGS

FIG. 1A is a perspective view of a waste management system.

FIG. 1B is a perspective view of the proximal end of the system of FIG. 1 with the waste transport device separated from the waste collection device.

FIG. 2B is a longitudinal cross-sectional side view of a distal end of FIG. 2A.

FIG. 2G is a top view of FIG. 2B.

FIG. 2H is a side view of FIG. 2B.

FIG. 2I is an axial cross-sectional view of a section of a waste transport device.

FIGS. 3A-D illustrate stages of deflation and folding of a retention cuff of a waste transport device.

FIG. 6 is a cross-sectional view of one embodiment of a single piece collection member and sphincter section.

FIGS. 7A-B are perspective views of another embodiment of a single piece collection member and sphincter section.

FIG. 7C is a perspective view of one embodiment of a retention cuff.

FIGS. 11A-D are perspective views of another embodiment of a connection system for a waste management system.

FIGS. 19A-B are perspective views of still another embodiment of an insertion device for a waste management system.

FIGS. 20A-C are perspective views of another embodiment of an insertion device for a waste management system.

FIG. 21 is a perspective view of another embodiment of an insertion device for a waste management system.

DESCRIPTION

Figure 2A:
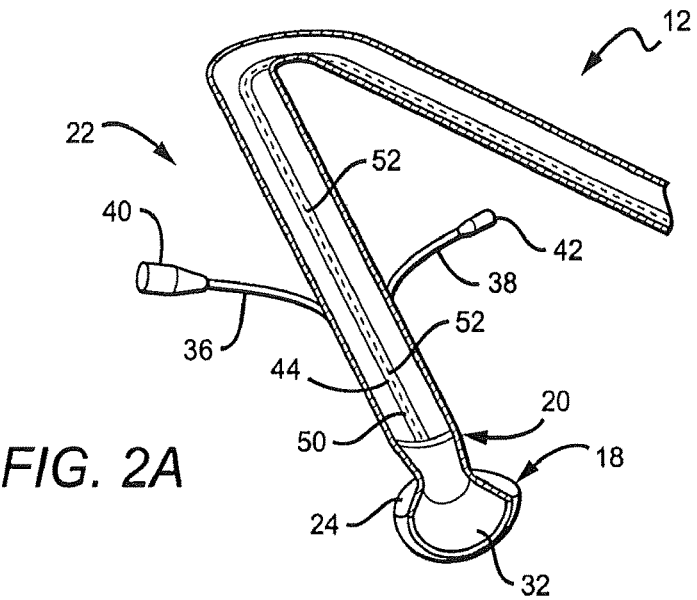
FIG. 2A is a longitudinal cross-sectional perspective view of a distal section of a waste transport device.

The following description should be read with reference to the drawings, in which like elements in different drawings are identically numbered. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. Also, as used herein, the terms "patient", "host" and "subject" refer to any human or animal subject and are not intended to limit the systems or methods to human use, although use of the subject invention in a human patient represents a preferred embodiment.

The waste management system described herein generally includes a waste transport device and a waste collection device. The waste transport device includes a distal end section, referred to herein as "the rectal section," configured for disposition in a patient's rectum to begin transport of fecal material from a patient to a waste collection device; a section proximal of the rectal section, referred to herein as "the sphincter section," configured for disposition in a patient's anal canal; and a section proximal of the sphincter section, referred to herein as "the extracorporeal section," having a majority of its length outside of the patient. The proximal end of the waste transport device is configured to connect to a waste collection device, including a collection container. In certain embodiments, the waste management system includes a connection system for selective coupling of the waste transport device to the waste collection device and/or an insertion device to facilitate insertion of the waste transport device into a patient. Embodiments of these and other features of a waste management system are described herein.

With reference to FIG. 1A, a waste management system 10 includes a waste transport device, including a generally tubular body (e.g., catheter) 12, having a distal end 14 and a proximal end 16, and a waste collection device, including a collection container 30. Positioned at the distal end 14 of the body 12 is a rectal section 18, including a collection member 32 and a retention cuff 24 disposed about an outer surface of the collection member 32 (FIG. 2). Proximal of the rectal section is a sphincter section 20, particularly adapted for disposition in the anal region of a patient, and an extracorporeal section 22 generally positioned outside of the patient's body when the system is in use (although a portion thereof may be inside). In one embodiment, the collection member 32, sphincter section 20 and extracorporeal section 22 are made of a material (e.g., silicone) with the same durometer (e.g., about 50 Shore A), while the retention cuff 24 is made of a material (e.g., silicone) with a different durometer (e.g., about 35 Shore A). In another embodiment, each of the aforementioned components are made of a material (e.g., silicone) with the same durometer (e.g., about 50 Shore A). A body connector 26 is coupled to a proximal end of the extracorporeal section 22 and is configured for quick, secure coupling to a collection container connector 28 to place the body 12 in fluid communication with a collection container 30. Various examples of connector embodiments are described in detail below. The body 12 generally has a plurality of lumens extending along at least a portion of its length, including, for example, a central lumen 34 for passage of fecal material from the patient to the collection container 30, an inflation lumen 36, a sampling lumen 38, and a flush lumen 44, each of which is discussed in detail below.

With reference to the rectal section 18 of the body 12, shown in FIGS. 2A-2B, the collection member 32 has a distal opening 31 that, when positioned for normal use, opens into the rectum of a patient, and a proximal opening 33 that connects to the sphincter section 20. In one embodiment, the proximal opening 33 has a cross-sectional area that is less than a cross-sectional area of the distal opening. For example, the proximal opening 33 may have an inner diameter less than the inner diameter of the distal opening 31. Such a configuration imparts to the collection member 32 a tapered shape (e.g., a funnel), which is believed to aid in the flow of waste material from the patient into the body 12. It is noted that the tapered shape according to one embodiment is a frusto-conical shape. In one embodiment, the collection member 32 is formed from one or more materials having a durometer sufficiently hard to prevent premature closure of the distal opening 31, thereby permitting safe passage of fecal material from the patient regardless of forces acting on the collection member 32. For example, the collection member may be made from a material selected from polyurethane, silicone rubber, natural rubber latex, synthetic rubber, guayule rubber, 80 SH polydimethylsiloxane, fumed silica, polyvinyl chloride (PVC), and combinations thereof. In one embodiment, the collection member 32 includes an annular ring disposed on the distal end thereof, the annular ring including a plurality of openings about its perimeter, which are connected to lumens through a wall of the collection member that may connect to one or more lumens disposed in the sphincter section and/or extracorporeal section. For example, the lumens through the wall of the collection member could extend through the sphincter section, all of which could connect to the sampling lumen 38.

In one embodiment, the rectal section 18 includes a split valve/baffle configured to control the type of fluid permitted to pass therethrough. For example, the baffle in one embodiment is configured such that an infusion of medication into the rectum will not open (e.g., flow through) the baffle, but a greater volume of fecal material will open (e.g., flow through) the baffle. In one embodiment, the baffle includes a plurality of discs extending alternately from different sides of a passage of the rectal section 18 (e.g., the collection member 32) such that the area open for fluid flow is spaced apart therealong. Thus, the medication intended for the patient will remain for a longer period within the rectum. In another embodiment, a duckbill valve is included in the rectal section 18 to control fluid flow therethrough.

In the embodiment shown in FIGS. 2A-2B, the retention cuff 24 is disposed about and attached to an outer surface of the collection member 32 and includes an inflatable balloon (e.g., conventional or non-conventional). In some embodiments, the balloon 24 includes a drug, such as a pain relief drug (e.g., lidocaine). The drug may be coated on a surface of the balloon 24 and/or may be incorporated in an inflation liquid (e.g., lidocaine mixture) such that the drug gradually diffuses through a wall of the balloon 24. In one embodiment, the retention cuff 24 includes a balloon, an outer surface of which is coated with lidocaine, and which is inflated following insertion into the patient with a lidocaine or a mixture including lidocaine. Surfactants and antimicrobial lubricant coatings may also be disposed on the retention cuff. Also, a retention cuff balloon may be encased or otherwise associated with a foam to maintain the rectal section in its deployed position within the patient's rectum and to prevent leakage. The foam may include an absorbant material and/or a coating to reduce odor. In one embodiment, a relatively high viscosity foam is used to inflate the retention cuff, following introduction into the rectum.

Figure 2C:
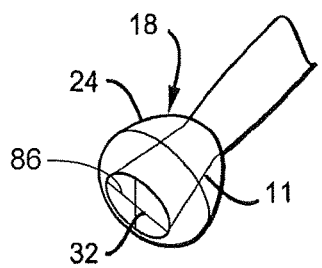
FIG. 2C is a perspective view of one embodiment of a retention cuff for a waste transport device.
Figure 2D:
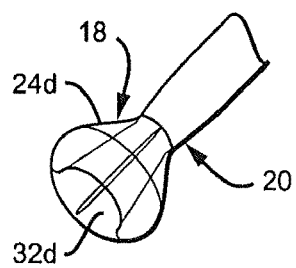
FIG. 2D is a perspective view of another embodiment of a retention cuff for a waste transport device.
Figure 2E:
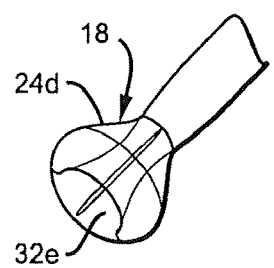
FIG. 2E is a perspective view of yet another embodiment of a retention cuff for a waste transport device.

FIGS. 2C-2E illustrate embodiments of the rectal section 18 with a retention cuff 24 and a collection member 32. FIG. 2C is similar to FIG. 2A, including a collection member 32 with a frusto-conical shape having a smooth continuous wall (e.g., no pleats or divisions between the proximal and distal openings) and a retention cuff 24 that when inflated creates a shoulder 11 at the junction between the cuff 24 and the body (e.g., sphincter section 20). FIG. 2C also illustrates a valve 86 configured to open when contacted by fecal material, but to remain closed when contacted by fluids infused into the patient. FIG. 2D shows a cuff 24 *d* with a geometry that more gradually transitions to the body, the collection member 32 *d* having a bell-shaped configuration (i.e., frusto-conical shape with a flared distal opening) with a smooth continuous wall. FIG. 2E shows cuff 24*d* surrounding a collection member 32*e* that has a trumpet-shaped configuration (i.e., a frusto-conical shape with curved sides and a flared distal opening) with a smooth continuous wall. The retention cuff in some embodiments, may also include one or more structural features as described more completely below in connection with FIGS. 5A-5D. Also, the retention cuff may have a tapered shape when inflated such that the diameter or perimeter increases from a proximal end to a distal end.

FIGS. 3A-3D illustrates one embodiment of a rectal section 18 with a retention cuff balloon 24, configured to provide an advantageously small profile for insertion. FIG. 3A illustrates the cuff 24 in its inflated state. FIG. 3B illustrates the beginning of deflation, showing the configuration of the cuff 24, which includes pockets 24' disposed between spaced apart raised sections 24" about the circumference of the cuff 24. FIG. 3C illustrates further deflation of the cuff 24 as the raised areas 24" collapse into the lumen of the rectal section 18, the cuff easily folded by bringing together the raised sections 24", as illustrated in FIG. 3D. It is noted that any of the retention cuffs 24 described herein may have a similar configuration to provide a small profile for insertion.

Figure 4A:
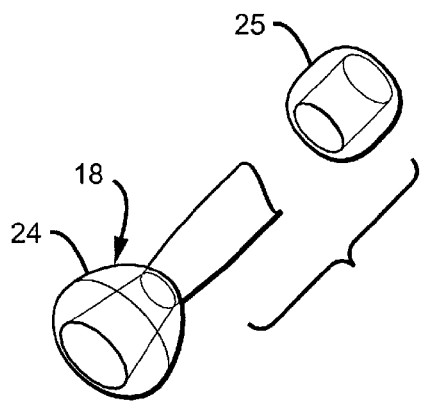
FIG. 4A-B are perspective views of a waste transport device with a proximal cuff.
Figure 4B:
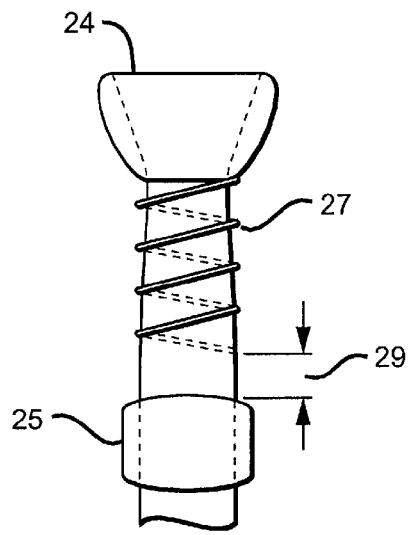

FIGS. 4A-4B illustrate embodiments including a proximal cuff 25, shown generally in FIG. 4A. The proximal cuff 25, which can include an inflatable balloon, is mounted to the body 12 proximally from the retention cuff 24, for example, along the extracorporeal section 22. Thus, when the body 12 is properly inserted, the proximal cuff 25 may be located between the patient's buttocks. The proximal cuff 25 is adapted to prevent upward migration of the retention cuff 24 when inserted and deployed in a patient's rectum and may optionally include anti-odor, moisturizer and/or lubricant coatings. In one embodiment, the proximal cuff has the form of an umbrella, cone, basin, etc. with the wide part facing the retention cuff in order to capture material that may leak from around the body. The cuff in such an embodiment may be made of a soft, absorbent material and is configured to be removable from the body in order to replace when necessary, or alternatively may be made of a material that is easily cleaned, such as, for example, a soft plastic material.

FIG. 4B illustrates a variation of a distal section of a body 12, which includes a retention cuff 24 and a proximal cuff 25 with a tension member 27 disposed in the wall of the body (e.g., along a portion of the sphincter section 20) between the cuffs 24, 25. The tension member 27 may include one or more elongated members embedded in the wall of the sphincter section and/or coupled to an inner or outer wall thereof. The tension member may include spaced apart longitudinally oriented members, circumferentially oriented members, helically arranged members, combinations thereof, etc. According to one embodiment, however, the tension member 27 is a helical coil made of shape memory material (e.g., Nitinol). Adjacent the proximal cuff 25, a sphincter section 29 free of the tension member is provided to prevent loss of sphincter tone as discussed above.

The tension member 27 has a collapsed configuration with a collapsed perimeter and an expanded configuration with an expanded perimeter greater than the collapsed perimeter. In one embodiment, at least a portion of the tension member 27 is disposed adjacent the retention cuff 24 such that when the retention cuff 24 is inflated, the tension member expands from the collapsed perimeter to the expanded perimeter. Following inflation of the retention cuff 24 and expansion of the tension member 27, the proximal cuff 25 is inflated. Due to the shape memory material, the tension member 27 will attempt to return to its collapsed configuration, which due to the connection to the retention cuff 24 will be resisted. This resistance provides tension between the cuffs 24, 25, which is believed to aid in the prevention of leakage and migration of the distal end of the body 12.

Figure 4C:
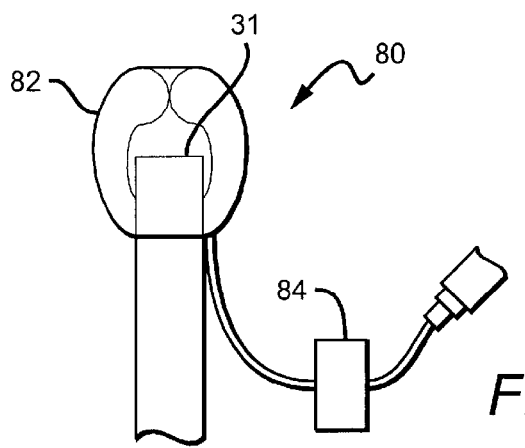
FIG. 4C is one embodiment of an inflatable retention cuff.

FIG. 4C illustrates one embodiment of an inflatable retention cuff that is adapted to occlude the distal opening 31 when activated. Occluding the lumen 34 of the body 12 may be desirable, for example, to temporarily block reflux and to retain medicants or drugs in the rectal vault. Known systems accomplish the occlusion function by including an internal balloon in the distal end of a catheter. The presence of an internal balloon may partially block the lumen of the catheter even when not inflated and/or may provide a surface for which fecal material adheres to, resulting in build-up and eventual blockage of the lumen. In the embodiment of FIG. 4C, instead of an internal balloon, retention cuff 80 includes a plurality of lobes 82 that may be expanded from a first inflated configuration, similar to the retention cuff 24 described above, to a second inflated configuration (as shown), converging to cover the distal opening 31 or otherwise block fluid from reaching the distal opening 31. The expansion from the first inflated configuration to the second inflated configuration can be accomplished by an infusion system 84 that indicates to the user the state of the retention cuff 80 (i.e., deflated, first inflated configuration, second inflated configuration) based on a pressure reading of the cuff 80. For example, the infusion system 84 could provide a readout of a first volume (e.g., 50 mL) when the lobes 82 are in the first inflated configuration and a second volume (e.g., 150 mL) when the lobes 82 are in the second inflated configuration. In another embodiment, a sliding cuff or sleeve may be positioned proximal of the retention cuff 80, the sliding cuff including arms or surfaces configured to force the cuff 80 inward upon contact therewith such that the distal opening 31 is occluded when the sliding cuff impinges on the retention cuff. Thus, for example, after the retention cuff 80 has been inflated to the first inflated configuration, the sliding cuff is moved distally at least partially over the retention cuff 80 to occlude the opening 31. Thereafter, when it is desired to remove fecal matter from the rectum, the sliding cuff is moved proximally out of contact with the retention cuff 80 so that the distal opening 31 is no longer occluded.

Figure 5A:
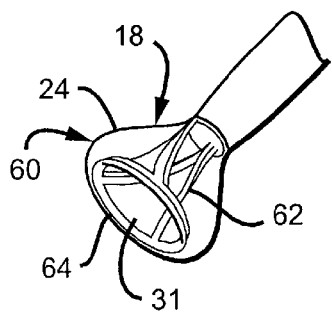
FIGS. 5A-D are perspective views of different embodiments of a collection member.

FIGS. 5A-5D illustrate different embodiments of the collection member. FIG. 5A illustrates a collection member 60 with a plurality of spaced apart struts 62 attached at their distal end to a ring 64, which defines the distal opening 31. The three struts 62 in the embodiment shown are twisted to facilitate collapse of the retention cuff 24 for insertion and removal of the body from the patient. The proximal end of the struts 62 may be coupled to the body just proximal of the rectal section 18 (e.g., sphincter section 20) or may extend further along a length of the body (e.g., through at least a portion of the extracorporeal section 22) to provide structural support thereto. The struts 62 may be embedded in the wall of the body section(s) or may be coupled to a surface thereof. In the rectal section 18, the twisted struts 62 may, together with the retention cuff 24, define the collection member lumen. Alternatively, the collection member lumen may be defined by another member (e.g., a tapered extrusion) to which the struts 62 are attached. The struts 62 and ring 64 may be formed from a metal, polymer, or other suitable material that provides structural support to the rectal section 18, and may have a circular cross-sectional shape, rectangular cross-sectional shape, or any other geometric cross-sectional shape.

Figure 5B:
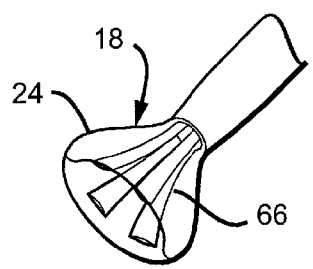
Figure 5C:
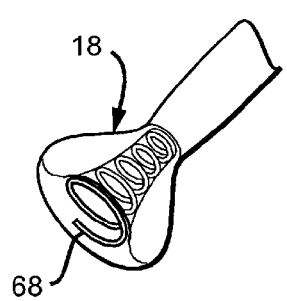
Figure 5D:
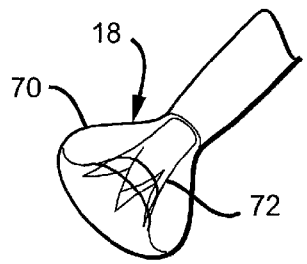

FIG. 5B is another embodiment of a collection member with a plurality of spaced apart struts (e.g., four), the struts 66 remaining untwisted (e.g., substantially aligned along a longitudinal axis) and attaching distally to the cuff 24 rather than a ring. Of course, a ring could also be included and/or a further member as described above in connection with FIG. 5A. The struts 66 have an increasing cross-sectional area from the proximal end to the distal end and in the embodiment shown transition from a circular cross-sectional shape at the proximal end to an oval cross-sectional shape at the distal end. Other cross-sectional shapes are also possible, such as those described above in connection with FIG. 5A, and are within the scope of the invention. FIG. 5C is an embodiment of a collection member including a helically arranged elongate member in the form of a coil 68. The coil 68 defines a lumen along a longitudinal axis thereof and may be attached directly to the cuff 24 or an additional tapered member. In one embodiment, the elongate member forming the coil 68 is hollow and is attached directly to the sampling lumen 38 to provide access to the patient's rectum for infusion of drugs/fluids and/or extracting samples for testing. FIG. 5D is yet another embodiment of a collection member. Collection member 70 has distal sections removed to facilitate collapse of the rectal section for insertion and removal. In the embodiment illustrated, the removal of sections results in a plurality of petals 72 evenly spaced apart about the circumference of the collection member 70. It should be noted, however, that many other types of patterns, including non-uniform patterns, are also contemplated herein and within the scope of the invention.

With further reference to the embodiment shown in FIGS. 2A-2B, the sphincter section 20 is disposed between the collection member 32 and the extracorporeal section 22. The sphincter section 20 in one embodiment is distinct from the extracorporeal section 22 and/or the collection member 32 in that the sphincter section is configured to collapse under lower pressures to preserve the tone/strength of the sphincter when positioned in the patient for extended periods. For example, in one embodiment, the material for the collection member 32 and sphincter section 20 are the same, but the thickness of the wall of the sphincter section 20 is less than the wall of the collection member 32. In other embodiments, the material for the sphincter section 20 is different from the material for the collection member 32 (e.g., more compliant, softer durometer, etc.) In one embodiment, the sphincter section 20 is made from a material selected from polyurethane, silicone rubber, natural rubber latex, synthetic rubber, 80 SH polydimethylsiloxane, fumed silica, polyvinyl chloride (PVC), and combinations thereof.

The shape of the sphincter section 20 may have a cross-sectional shape that transitions from a distal end 21 to a proximal end 23, such as shown in FIGS. 2A-2B and 2F-2H. For example, the sphincter section 20 in the embodiment shown has a substantially circular cross-sectional shape at its distal end 21 and an oval cross-sectional shape at its proximal end 23 that attaches to the extracorporeal section 22. In other words, at its proximal end 23, the sphincter section 20 has a larger diameter along a first axis (i.e. the z-axis shown in FIG. 2B), than along a second axis orthogonal to the first axis (i.e. the y-axis shown in FIG. 2B). The oval proximal end 23 of the sphincter section matches the oval distal end of the extracorporeal section 22 (FIG. 2I), which in one embodiment maintains this oval cross-sectional shape from the distal end to the proximal end. The transitional shape for the sphincter section 20 is advantageous for resisting rotational motion. That is, the sections of the system that have oval cross-sections (e.g., the sphincter section proximal end 23 and the extracorporeal distal end) are more resistant to rotation than sections with circular cross-sections (e.g., the sphincter section distal end 21 and the collection member proximal end 33). In one embodiment, the sphincter section 20 has an hourglass shape. As with the embodiment of FIGS. 2A-2B and 2F-2H, the proximal end of the sphincter section 20 may have an oval cross-sectional shape, while the distal end may have a circular cross-sectional shape. Alternatively, each of the proximal and distal ends of the sphincter section may have a circular cross-sectional shape to match circular cross-sectional shapes of the distal end of the extracorporeal section and the proximal end of the rectal section, respectively.

In one embodiment, the sphincter section 20 includes a sealing feature, such as a plurality of ribs arranged about the perimeter thereof. The ribs may be spaced apart and inflatable such that the ribs are deflated for insertion and inflated upon deployment. When inflated, the ribs may provide a seal and/or prevent rotational movement of the sphincter section 20. The ribs may be arranged substantially parallel to a longitudinal axis of the sphincter section 20, circumferentially about the perimeter of the sphincter section 20, diagonally, helically, combinations thereof, etc. In one embodiment, anti-twist rings are disposed about sections of the distal end of the system, such as the sphincter section and the distal end of the extracorporeal section 22. The rings may be longitudinally spaced from one another and may be inflatable similar to the ribs. The rings and/or ribs may be incorporated along the distal end of the system to provide an anti-rotating function. Further, the rings and/or ribs may include a reinforcing feature, such as a hard material (e.g., wire), to prevent collapse of the system lumen transporting fecal material from the patient. In one embodiment, a stiff tube or coiled, flexible spring is disposed in a wall of a section of the waste transport device or along an internal surface thereof.

With reference to FIGS. 2B and 2I, inflation lumen 36 and irrigation/sampling lumen 38 can be located adjacent and parallel to lumen 34 and on opposite sides thereof. The inflation lumen 36 and the irrigation/sampling lumen 38 can each be a flexible cylindrical tube extending along and integrally molded with, embedded into, or otherwise attached to an inner surface of at least a portion of the rectal section 18, sphincter section 20 and extracorporeal section 22. The distal end of the inflation lumen 36 is in fluid communication with the interior of the retention cuff balloon 24, while the proximal end of the inflation lumen 36 diverges from the extracorporeal section 22 outside of the body when the system is properly inserted. An inflation port 40 is attached to the proximal end of the inflation lumen and may include a luer-style connector for connection to a syringe or other device for selectively inflating and deflating retention cuff balloon 24. The distal end of the irrigation/sampling lumen 38 extends through the rectal section 18 and has a distal opening positioned adjacent the distal opening 31 of the collection member 32 so that fluids may be drawn from the patient therethrough. The proximal end of the irrigation/sampling lumen 38, similar to that of the inflation lumen, diverges from the extracorporeal section 22 and terminates at an irrigation/sampling port 42. The port 42 may similarly include a luer-style connector for connection to a syringe or other device so that, for example, a medication or irrigant may be infused into the patient's rectum, or a fecal matter sample may be extracted from the patient's rectum. In one embodiment, both the inflation lumen 36 and sampling lumen 38 are polyurethane or silicone tubes, having sizes in the range of about 5 Fr to about 10 Fr, for example, a 6 Fr inflation lumen and an 8 Fr sampling lumen.

Figure 2F:
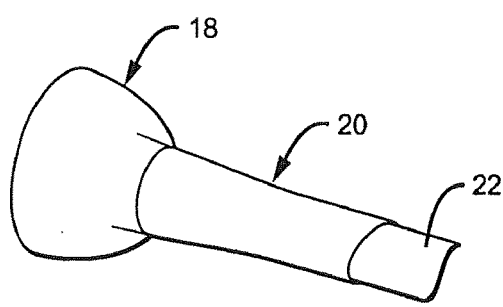
FIG. 2F is a perspective view of FIG. 2B.

Also, as seen best in FIGS. 2A and 2F, the extracorporeal section 22 can include a flush lumen 44 disposed along a length of the extracorporeal section 22 in parallel with the central lumen 34. The flush lumen 44 is configured to flush and clean the central lumen 34 as necessary. For example, it may be desired to periodically flush the lumen 34 of the body 12 in order to prevent bacterial contamination and to also aid in reduction of odor due to fecal build up. In one embodiment, the flush lumen 44 is closed at a distal end (e.g., the distal end of the extracorporeal section 22) and connects at a proximal end to a flush port 46 coupled to, and extending through, a wall of the extracorporeal section 22 (FIG. 1) that provides access for a syringe or other device for inputting a desired cleansing fluid into the flush lumen 44. A port cover 48 (FIG. 1) of any suitable variety may be used that is configured to sealably close and open the flush port 46. Referring to FIG. 2A, to facilitate flushing of the central lumen 34, the flush lumen 44 can be perforated with a plurality of apertures 50 positioned along the length of the flush lumen 44. In one embodiment, the apertures 50 are grouped into aperture groups 52, such as groups of four, spaced from one another along the length of the flush lumen. The apertures may be arranged substantially linearly, as shown, or may be otherwise disposed, for instance, in circular patterns, along separate or continuous curves, etc.

The collection member 32 and sphincter section 20 may be formed together into a single piece, such as member 120, shown in FIG. 6. Member 120 includes a collection member 32 that is unattached to the sphincter section 20 at its proximal end, the attachment occurring only at a distal end where the member 120 forms a rolling portion 122. Thus, the wall 121 defining the lumen through member 120 extends from a proximal end 118 to the distal end of the collection member 32, turning back at the rolling portion 122 toward the sphincter section 20, and terminating at a distal end 119 where it attaches to a proximal end of a retention cuff 24 (the retention cuff 24 having a distal end attached adjacent to the rolling portion 122). This configuration permits free motion and movement of the sphincter section 20 with respect to the retention cuff 24 such that the cuff is not significantly displaced (if at all) when the sphincter section 20 is twisted (as represented by arrow 8 and the dotted lines) or pulled axially, thereby isolating potential loads from the retention cuff 24, rather than transferring loads thereto. Applicants believe that by generally preventing the transfer of loads from proximal sections of the waste transfer member to the retention cuff, several benefits may be realized, such as, for example, minimization of leakage around the retention cuff and minimization of pressure exerted on the rectal vault (thereby reducing the incidence of pressure necrosis).

Further, a distal-only attachment configuration enables movement of a tool 112 over the length of the member 120 to facilitate insertion and removal of the waste transport device, as well as "milking" of the collection member 32. In particular, a tool 112 may include an end piece 116 coupled to an elongate member 114, the end piece 116 having a cross-section similar to the cross-section of the member 120, a size less than that of the collection member 32 in its expanded configuration, and a rigidity greater than that of the collection member 32. For example, if the member 120 has a generally hourglass shape as shown in FIG. 7, the end piece 116 of the tool 112 can be circular with a diameter generally equal to the desired insertion diameter for the collection member 32. Thus, insertion is facilitated by merely pushing on the proximal end of the elongate member 114 such that a force is exerted on the rolling portion 122 from an inner surface thereof by the end piece 116, while the distal end of the collection member 32 is maintained in a collapsed configuration with a lower profile than that of the collection member in its expanded configuration. Following insertion, the tool 112 may be slid in a proximal direction while the member 120 is maintained in position in the patient to permit expansion of the collection member 32 to its expanded configuration. During use, the member 120 may be "milked" by sliding the tool 112 over the member 120 and performing successive axial movements, distal to proximal, to move the waste through the lumen of the member 120. To remove the waste transport device, the tool 112 is slid over the member 120 to the distal end rolling portion 122 in order to collapse the collection member 32 to the collapsed configuration having a suitable insertion/removal diameter.

In another embodiment, collection member 32 and sphincter section 20 are formed into a continuous member 90, shown in FIGS. 7A-7B. In the embodiment shown, member 90 includes a stiffening ring 92 around a circumference of the collection member 32 and relief sections 93 disposed approximately equidistantly between the inflation lumen 36 and the sampling lumen 38 to facilitate collapse of the collection member 32 for delivery and withdrawal from the patient's rectum. The relief sections 93 may be raised portions of the collection member inner surface, for example, having a semi-circular cross-section along its length. The distal end of the collection member includes a lip 96 about the circumference of the distal opening 31. Openings 94 in a wall of the collection member are configured to pass air or fluid from the inflation lumen 36 to a surrounding retention cuff (it is noted that the distal end of the inflation lumen shown open in these figures will be closed in a final assembly so that air or fluid will be forced out of the openings 94). The collection member 32 has a generally frusto-conical shape, while the sphincter section 20 has a generally cylindrical shape. FIG. 7C is one embodiment of a retention cuff 123, having a bulb-like geometry along a body 124 and a tapered distal end 125. The retention cuff 123 is configured to fit over the collection member 32 and is attached at distal end 125 to the distal end of the collection member 32 and at proximal end 129 to a proximal end of the collection member 32.

Figure 7D:
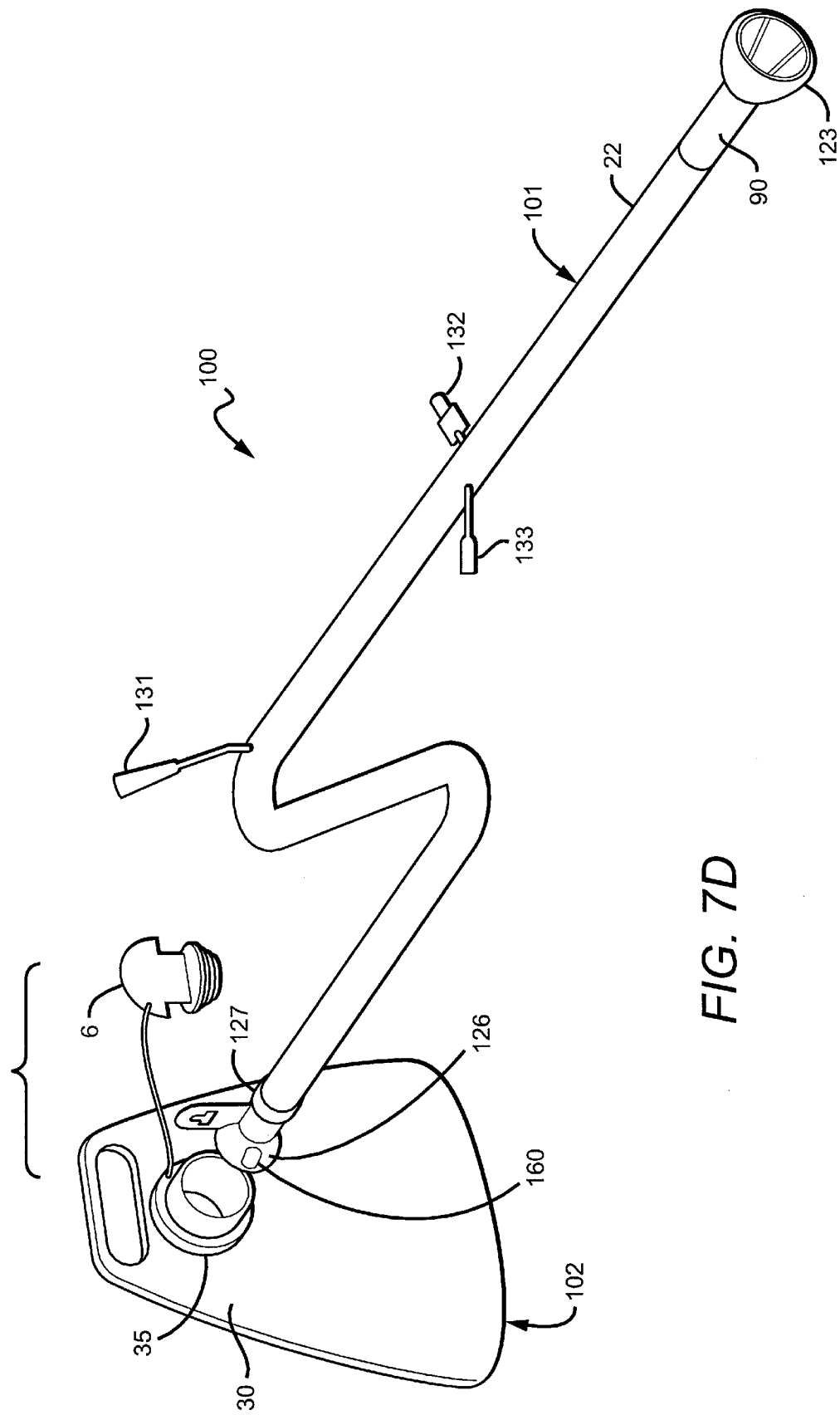
FIG. 7D is a perspective view of one embodiment of a waste management system.
Figure 7E:
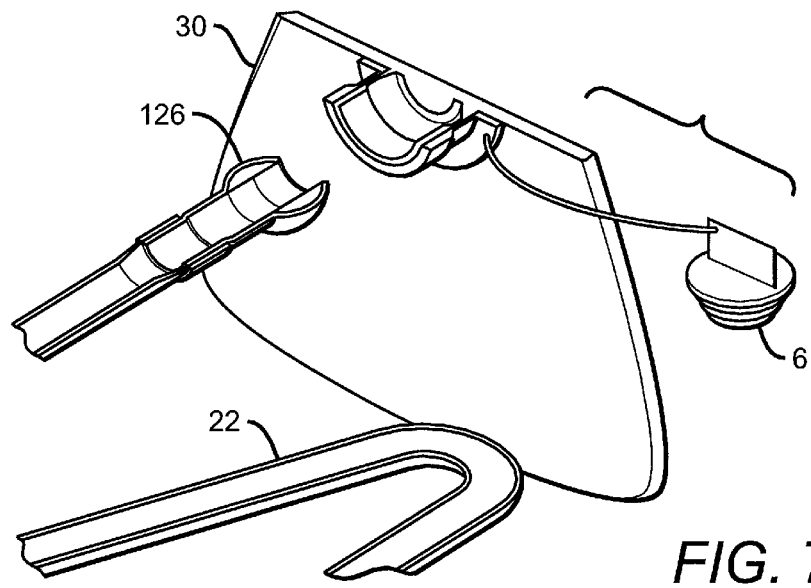
FIGS. 7E-G are cross-sectional views of different regions of the waste management system of FIG. 7D.
Figure 7F:
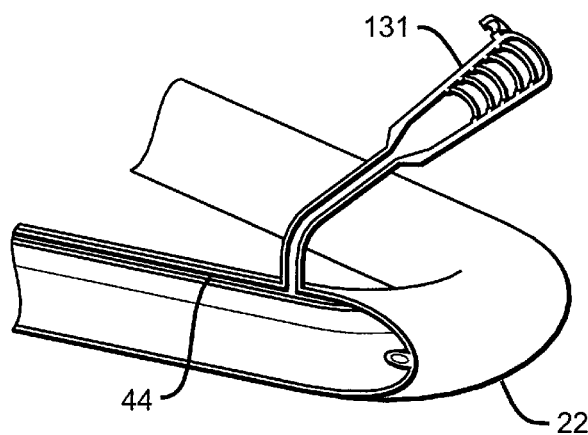
Figure 7G:
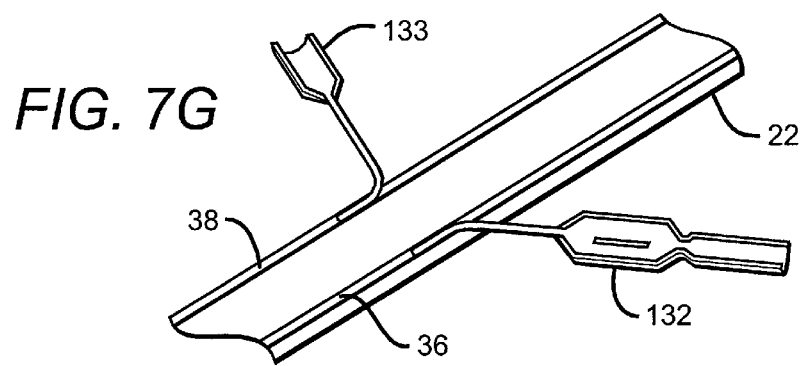

FIG. 7D illustrates one embodiment of a waste management system 100, including a waste transport device 101 and a waste collection device 102. Waste transport device 101 includes member 90 and retention cuff 123 of FIGS. 7A-C, an extracorporeal section 22, a connector housing 126, connector collar 127 and connector ball valve 160 (described in more detail below), and devices for fluid movement, including arm flush lumen 131, arm pilot balloon 132 and arm irrigation sleeve 133. Waste collection device 102 includes a collection container 30, a hub socket 35 configured to receive connector housing 126, and hub plug 6 tethered to the hub socket 35, the hub plug 6 including threads for mating with an interior threaded surface of hub socket 35 in order to seal the opening of the collection container 30. FIG. 7E is a cross-sectional view of the collection container interface, showing connector housing 126 and hub socket 35 in more detail. FIG. 7F is a cut-away view of arm flush lumen 131 and its connection to flush lumen 44 of extracorporeal section 22. FIG. 7G is a cross-sectional view of both the arm pilot balloon 132, connected to inflation lumen 36, and arm irrigation sleeve 133, connected to sampling lumen 38. It is noted that the hexagonal section of the arm pilot balloon is configured to bulge outward when there is line pressure to indicate such to the user.

Another embodiment of a waste management system is illustrated in FIGS. 8A-8D. Waste management system 110 includes waste transport device 111 with a relatively shorter length than waste transport device 101 and a waste collection device 109 with a different configuration than waste collection device 102. In particular, waste collection device 109 has a tubular shape with a proximal opening covered by a sealed septum 105. An odor control filter 106, made of a material such as carbon, may be embedded in the wall of the waste collection device 109 or may be a covering for a vent disposed therein. The waste collection device 109 may have a collapsed configuration which expands upon receipt of waste material therein, or may have a more rigid configuration (as shown) such that a vent in a wall thereof may enhance drainage efficiency.

The waste transport device 111 includes an extracorporeal section 22 with a drain tube irrigation port 95, an inflation port 107 and a sampling port 108. The inflation port 107 is connected to an inflation lumen 36 extending from the inflation port 107 to the retention cuff 24, while the sampling port 108 is connected to a sampling lumen 38 extending from the sampling port 108 to the distal end of the waste transport device 111. The irrigation port 95, as shown in FIG. 8D, is connected to a flush lumen 99 with patterned holes along its length to flush the lumen of the extracorporeal section 22. As fluid is introduced through the port 95, the fluid extends along the length of the flush lumen 99 entering into the lumen of the extracorporeal section 22 through the patterned holes. The irrigation port 95 in one embodiment is an EZ-LOK® Sampling Port. In another embodiment, an EZ-LOK® Sampling Port is also positioned on the extracorporeal section 22 with access to the lumen thereof for periodic sampling of fecal matter therefrom.

Figure 8A:
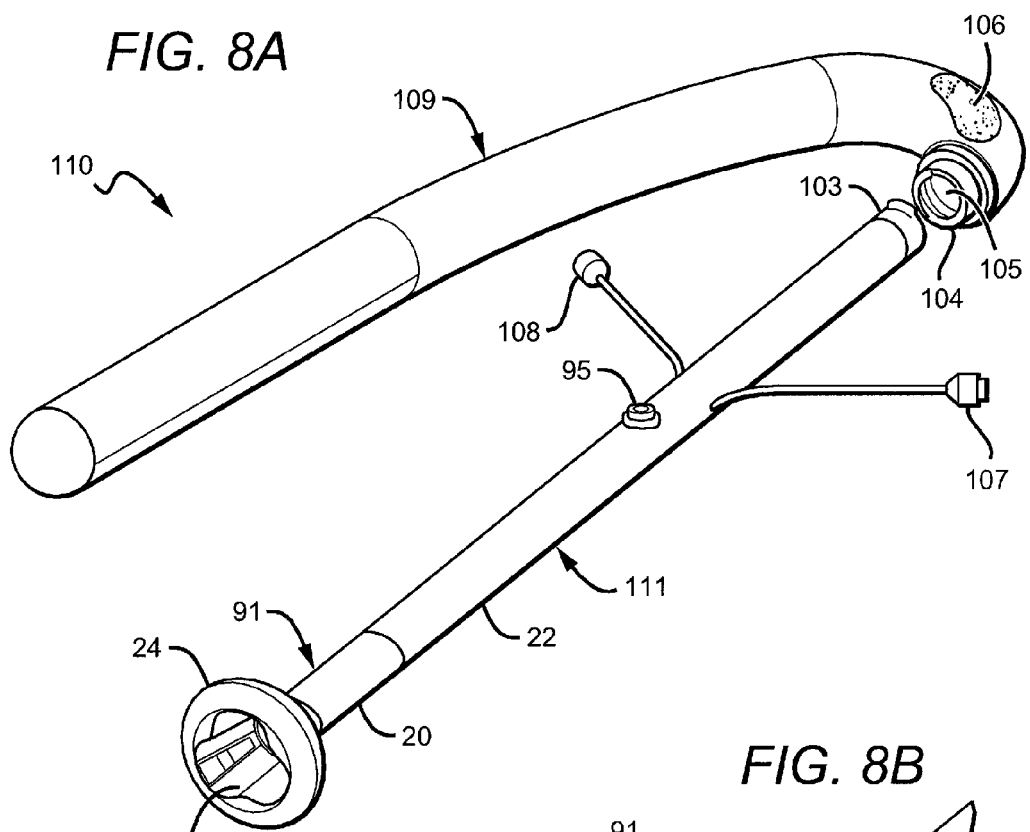
FIG. 8A is a perspective view of another embodiment of a waste management system.
Figure 8B:
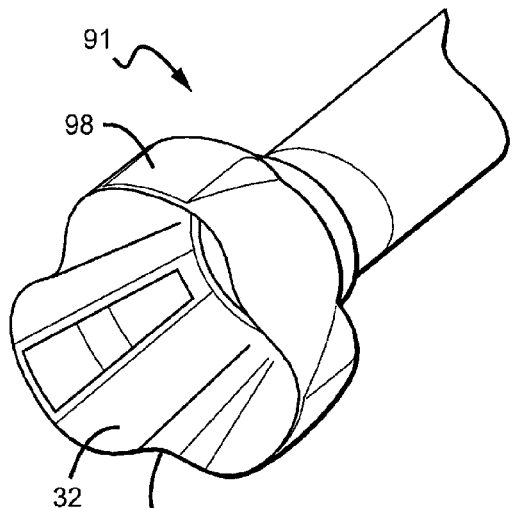
FIG. 8B is a partial view of a single piece collection member and sphincter section of the waste management system of FIG. 8A.
Figure 8C:
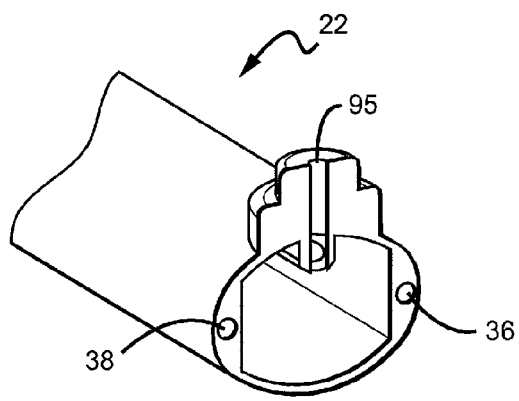
FIG. 8C is a cross-sectional view of the extracorporeal section of the waste management system of FIG. 8A.
Figure 8D:
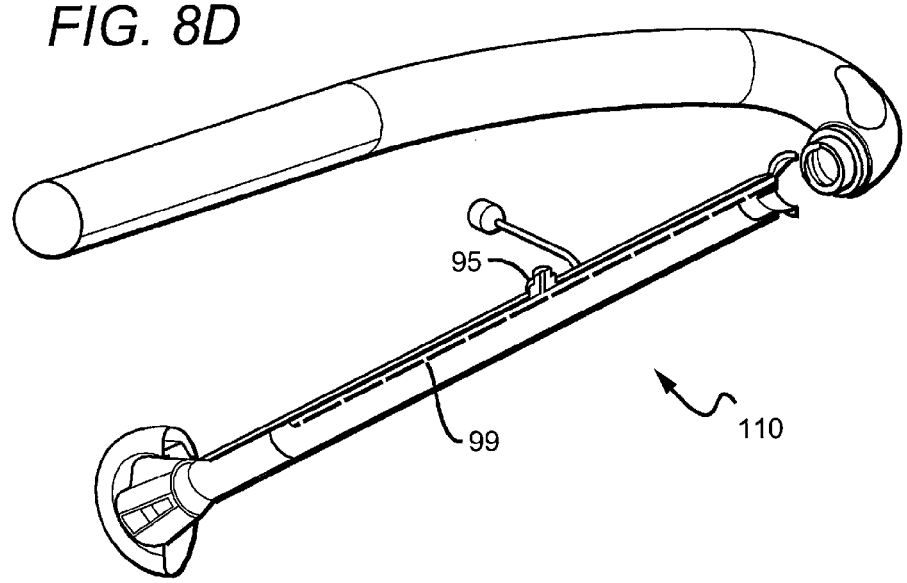
FIG. 8D is a cross-sectional view of the waste transport device of the waste management system of FIG. 8A.

As best seen in FIG. 8B, a continuous member 91 includes both the sphincter section 20 and collection member 32. The collection member 32 has a wavy perimeter with undulations including peaks and valleys. The valleys 97 form crease lines to facilitate collapse of the collection member 32 to a collapsed configuration. A retention cuff 24 surrounds the collection member 32. Collapsible struts 98 are positioned at the peaks of the perimeter, forming a stiffening area to resist collapse of the collection member during use. The struts 98, as shown, extend circumferentially away from the perimeter along an outer surface of the peak section and form a recessed region along an inner surface of the peak section of the collection member. Such a shape is designed to fit in an insertion tool such that collapse of the collection member is facilitated. In other embodiments, the struts 98 may take a different geometric shape or form, depending on the shape/size of the insertion tool and/or desired levels of stiffness for the collection member. The waste transport device 111 includes at its proximal end a connection member 103 configured for coupling to connection member 104 of the waste collection device 109, embodiments of which are described in more detail below.

In the embodiments described herein, the extracorporeal section 22 may have a uniform cross-section along its length (e.g., circular, oval, etc.) or a transitional cross-section similar to the sphincter section 20 shown in FIGS. 2A-2B. The extracorporeal section 22 can be formed of a non-collapsible tube constructed of a material that is sufficiently stiff in order to maintain its shape during use (e.g., to prevent or minimize kinking, to facilitate drainage, etc.), but soft enough to be "milked" by a care professional to force through fecal material when necessary. For example, in one embodiment, the extracorporeal section is made from a rubber or plastic material that does not collapse under its own weight. In one embodiment, the extracorporeal section 22 includes one or more stiffening structures, such as inflatable ribs, metal wires or ribbons, axially positioned rings, etc., to assist in preventing collapse of the lumen 34. As with the ribs discussed above, the stiffening structures may be disposed longitudinally, circumferentially, helically, etc.

The "milking" in one embodiment is performed by a clamp tool including opposing first and second arms attached to a handle, the first and second arms arranged approximately perpendicular to the handle with a gap therebetween. A portion of the sphincter section 20 or extracorporeal section 22 is placed between the arms and the handle is pulled in a proximal direction to move fecal matter through the section milked. The tool may include a locking feature such that the first arm locks or is coupled to the second arm to clamp a section of the waste transport device.

The body 12 can be secured to the collection container 30 via respective connectors 26 and 28. With reference to FIG. 1B, the collection container 30 is in the form of a bag, having an opening 54 located on a front side, which provides access to the interior thereof. In other embodiments, the collection container 30 may be in other suitable forms with one or more openings therein. Because it is desirable to secure the body 12 to the collection container 30 so that the central lumen 34 is in fluid communication with the interior of the collection container 30, the connection system positions the lumen 34 substantially in axial alignment with the opening 54 when the body 12 is coupled to the collection container 30. In one embodiment, the collection container 30 is configured to absorb and reduce odor, for example, by providing a ventable section including activated charcoal. The activated charcoal can be changed when desired via interchangeable charcoal cartridges that are inserted into the collection container 30. The collection container 30 can also have a parylene coating, anti-odor coating and/or antimicrobial coating. In addition, the collection container 30 can include material in a wall thereof that absorbs/binds odor. Suitable examples of coatings/materials include those disclosed in U.S. Pat. No. 6,579,539, U.S. Pat. No. 6,596,401, U.S. Pat. No. 6,716,895, U.S. Pat. No. 6,949,598, and U.S. Pat. No. 7,179,849, each of which is incorporated by reference in its entirety into this application.

In the embodiment of FIG. 1B, the collection container connector 28 includes a slide mechanism adapted to receive and retain an annular flange extending from the body connector 26. Accordingly, the body 12 can be secured to the collection container 30 by sliding the annular flange section of the catheter connector 26 into a slot or grooved section of the container connector 28. When it is desired to separate the body 12 from the collection container 30, the body connector 26 can be slid upwards, out of the container connector 28, thereby disengaging the body 12 from the collection container 30. Because it is often desirable to prevent leakage from the body 12 and the collection container 30 upon separation of the body 12 from the collection container 30, closures valves 56 and 58 can be provided in the proximal opening of each. In one embodiment, the closure valves 56 and 58 are split polymeric coverings, such as septums, that open when fluid pressure acts thereon from the fecal matter and/or flush lumen fluid in central lumen 34. In other embodiments, the valves open upon connection between the body 12 and collection container 30. For example, a mechanism on connector 26 and/or 28 will open one or both of the valves 56, 58 when the annular flange of the connector 26 is slid into the slot of the connector 28.

Figure 9A:
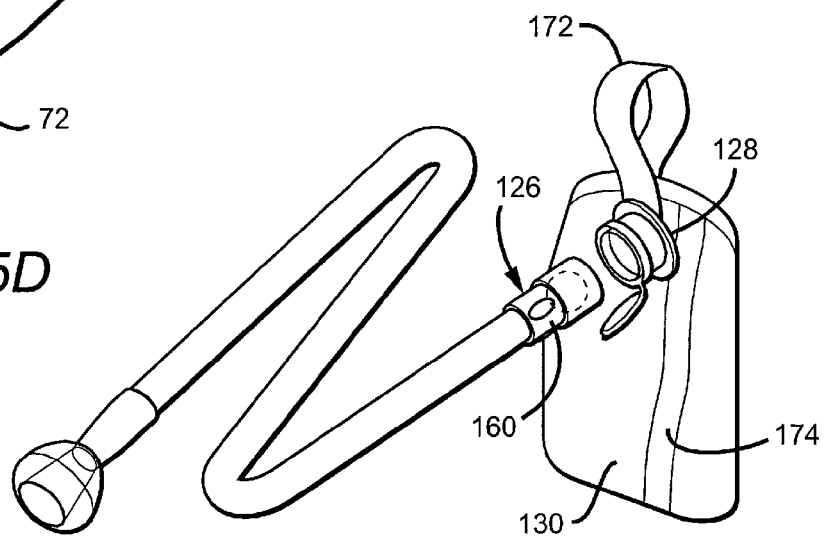
FIG. 9A is a perspective view of one embodiment of a waste management system with a valved connection system.
Figure 9B:
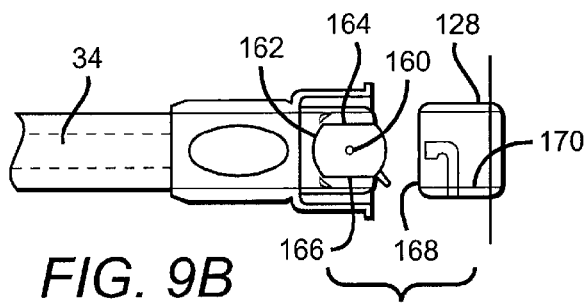
FIGS. 9B-D are enlarged views of the connection system of FIG. 9A at different stages of connection between the waste transport device and waste collection device.
Figure 9C:
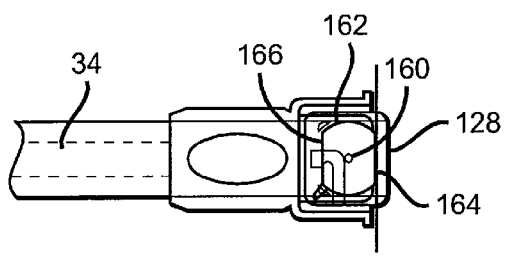
Figure 9D:
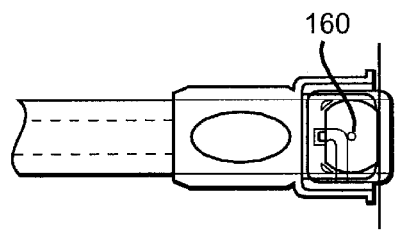

Another embodiment of a connection system for the waste management system is shown in FIGS. 9A-9D. A catheter connector 126 includes a ball valve 160 that is rotationally held in the catheter connector 126 and has an internal channel 162 extending between openings 164 and 166 located on opposite ends of the ball valve 160. A nub 168 extends from a portion of the ball valve 160. FIG. 9B shows the configuration of the ball valve 160 when the connector 126 is in a sealed position and separated from a collection container. Here, the openings 164 and 166 and the interior channel 162 do not align with the central lumen 34 of the catheter, thereby sealing the proximal opening of the body 12. However, in the open position, as illustrated FIGS. 9C and 9D, the ball valve 160 is rotated so that the channel 162 and openings 164 and 166 are aligned with the central lumen 34 when the connector 126 is connected to the collection container connector 128. A divot 170 located in the container connector 128 is configured to trap and move the nub 168 when the catheter connector 126 is secured to the container connector 128. As shown in FIGS. 9C and 9D, when the container connector 128 and the catheter connector 126 are brought together, the nub 168 is moved rearward, causing the ball valve 160 to rotate to its open position. In one embodiment, the connection between the body 12 and the collection container 130 is securely held together by a bayonet type mechanism or other types of known securing mechanisms.

As shown in FIG. 9A, the collection container 130 may include a strap 172 that can include hook and loop material, such as VELCRO® brand hook and loop material. The strap 172 can be adapted to be an effective handle and to securely hang the collection container 130 from a patient's bed. The strap 172 can be fastened at one end to the container connector 128 with a free end including a VELCRO® strip affixed to one side for engagement to a corresponding receiving strip affixed to a part of the strap adjacent the end fastened to the container connector 128. Thus, attachment to a patient's bed or other structure is easily accomplished by separating the free end of the strap 172 from the receiving strip, looping it through an opening in the structure, and reattaching the free end to the receiving strip. Alternatively, the collection container 130 may include a hook or other like member to hang the collection container 130 from the patient's bed. The collection container 130 may be substantially opaque with a transparent strip 174 extending from a lower portion of the container to an upper portion thereof. The transparent strip 174 can be located on multiple sides of the container (e.g. front, first side, second side and back), or only a single side as shown. The opaque portion of the container 130 substantially conceals the contents of the container, while the transparent strip 174 provides a means to visually monitor the volume of waste in the container so that it can be emptied before reaching a maximum level.

Figure 10A:
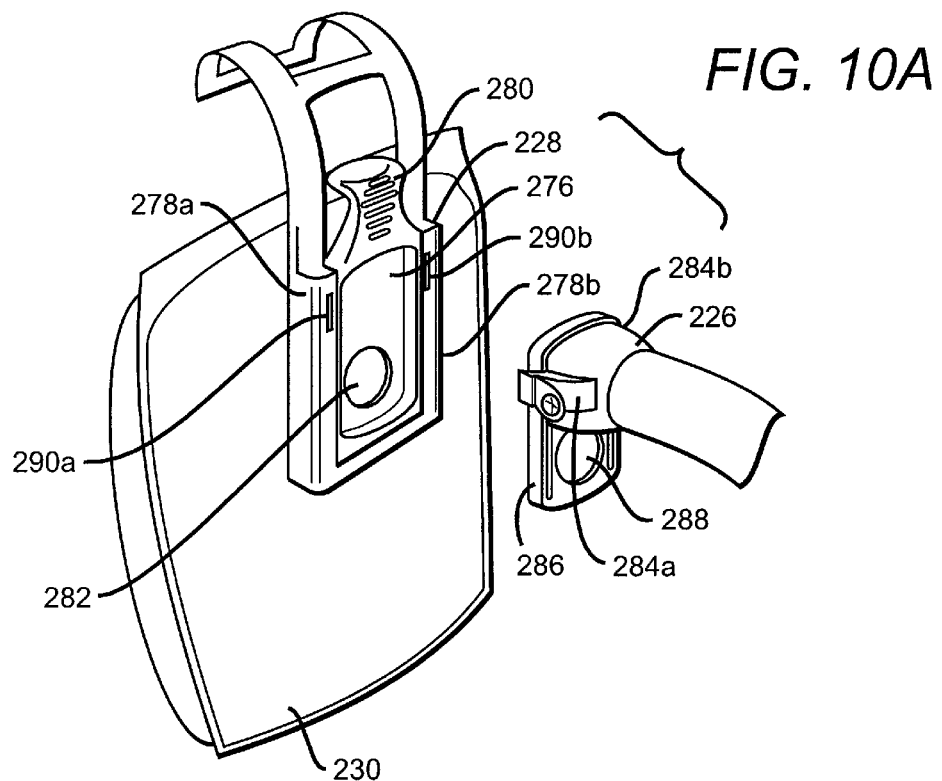
FIGS. 10A-B are perspective views of another embodiment of a connection system for a waste management system.
Figure 10B:
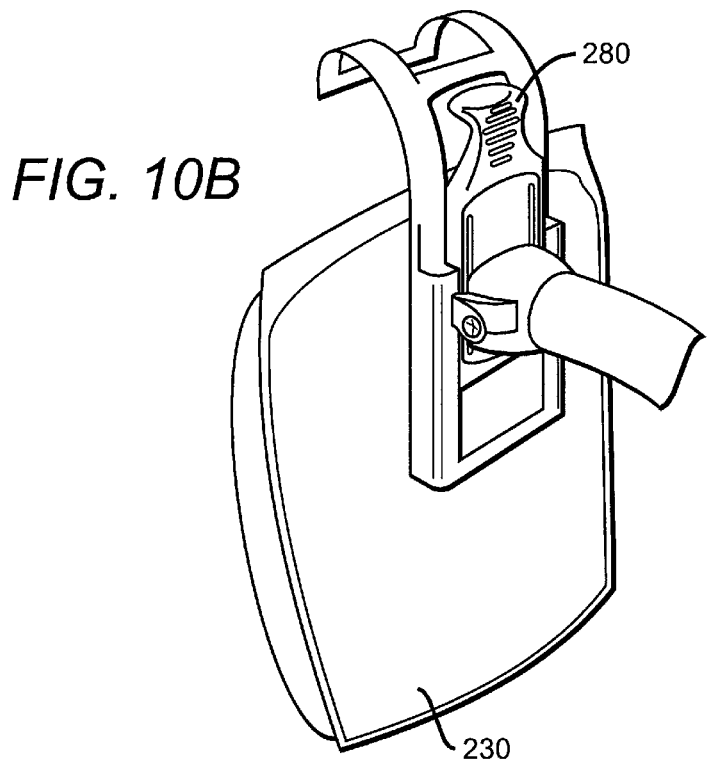

In another embodiment of a connection system for the waste management system, a guillotine connection assembly shown in FIGS. 10A-10E includes a body connector 226 and a container connector 228. The container connector 228 includes a first slide 276 held between two sidewalls 278a and 278b and moveable therealong. An upper end of the first slide 276 has a tab 280 for griping and a lower portion of the slide 276 includes an aperture 282. When the first slide 276 is in a closed position, as shown in FIG. 10A, a collection container opening is covered by the slide 276. The first slide 276 is moved upward to place in an open position, in which the slide aperture 282 is aligned with the collection container opening. The body connector 226 includes a pair of locking arms 284a and 284b extending from the sides of the connector 226. A second slide 286 is held between the locking arms 284a and 284b and includes an aperture 288 located on a lower portion thereof having approximately the same size and shape as the aperture 282 on the first slide 276.

To form a connection between the body 12 and the collection container 230, the second slide 286 is positioned such that the ends of the locking arms 284a and 284b are positioned adjacent corresponding slots 290a and 290b of the container connector 228 and the apertures 282 and 288 are aligned. The locking arms, which may include a feature that indicates a positive connection (e.g., tactile, audible, etc.), are then pressed into the slots 290a and 290b such that the body 12 is coupled to the collection container 230. The tab 280 is then pulled in an upward direction, causing both the first slide 276 and the second slide 286 to move into an open position, in which the lumen 34 of the body 12 is aligned with the collection container opening to place the collection container 230 in fluid communication with the body 12. In one embodiment, movement of the tab 280 in an upward direction locks the connectors 226, 228 together to prevent inadvertent separation during use. When it is desired to remove the collection container 230 from the body 12, the tab 280 is pushed in a downward direction, sealing both the opening of the collection container 230 and the opening in the body 12 and unlocking the connectors 226, 228 for separation. In one embodiment, the locking arms 284a and 284b include a clamping mechanism that can be opened by pressing a proximal end toward the connector 226 and closed by releasing the end. Thus, to release connector 226 from connector 228, the clamping mechanism on arms 284a, 284b is opened.

A variation of a guillotine connection assembly is shown in FIGS. 11A-11D. As seen in FIG. 11A, an ostomy bag flap seal 310 seals the opening of the collection container 330. A body connector 326 coupled to the body 12 includes a disk 312 positioned on a side of the connector 326 opposite the face that can be moved between a sealed position (shown in FIG. 11B) and an unsealed position (shown in FIG. 11C). Nubs 314a and 314b extending from opposing sides of the disk 312 are held in respective tracks 316a and 316b of the catheter connector 326, permitting the disk 312 to slide in upward and downward direction, as shown in various stages in FIG. 11D. When the catheter connector 326 is separated from a container connector 328, the disk 312 is in the sealed position. The connector 326 is attached to the container connector 328 by sliding the track of connector 326 over the rail of connector 328, by pressing the connector 326 onto the connector 328, or other manner of connection known to one skilled in the art. Following connection, the disk is pushed up the tracks 316a and 316b to unseal the body proximal opening and place the body 12 in fluid communication with the collection container 330. FIG. 11C illustrates an embodiment of a hook/handle 316 attached to the collection container 330, which may be integral with the collection container connector 328 and can serve to hold the collection container 330 on a patient's bed, as well as providing a handle for the collection container 330.

Figure 12:
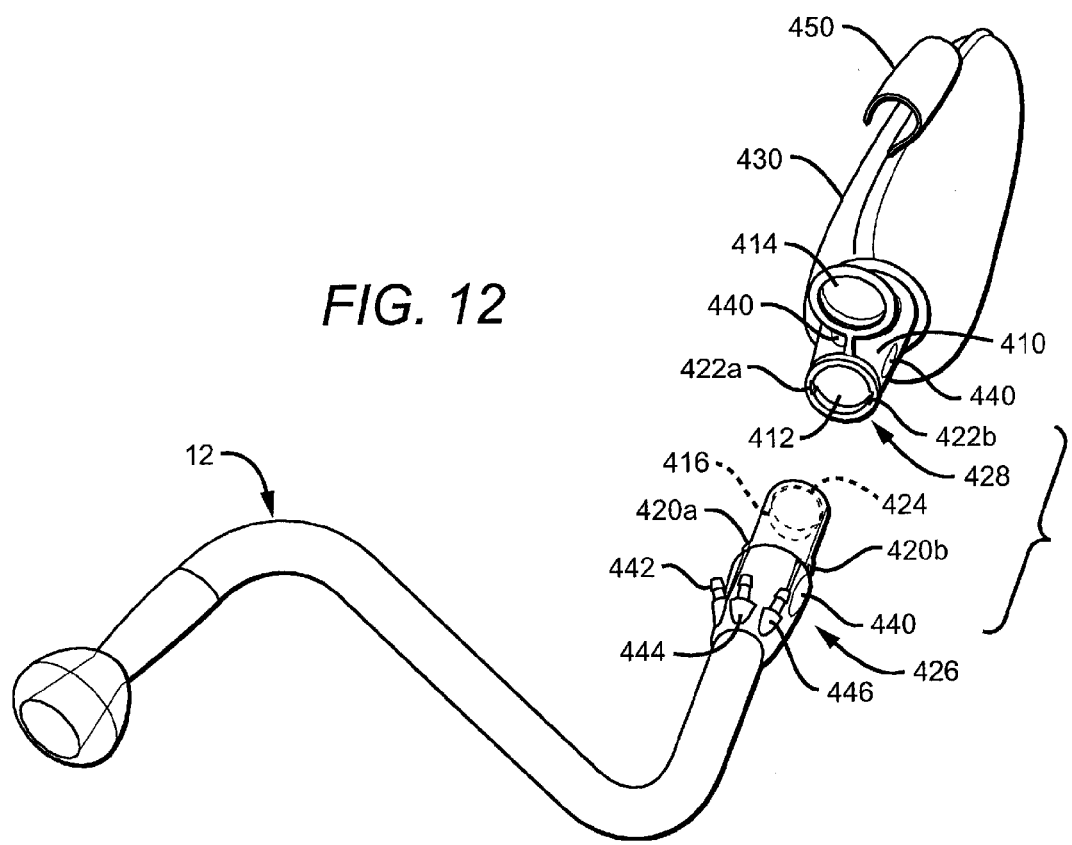
FIG. 12 is a perspective view of yet another embodiment of a connection system for a waste management system.

Yet another manner of connecting a catheter to a collection container is shown in FIG. 12. A container connector 428 attached to a collection container 430 includes a housing 410 having an opening 412 to the interior of the collection container and a cap member 414. The cap member 414 can be securely snapped onto the housing 410 over the opening 412 to seal the opening 412. A body connector 426 coupled to the body 12 includes a reduced diameter section 416 at its proximal end that is configured for insertion into the opening 412 of the container connector housing 410. Locking tabs 420a and 420b are located on opposite sides of the reduced diameter section 416 and are configured to slide into corresponding slots 422a and 422b extending along the interior of the container connector housing 410. When fully inserted, the locking tabs 420a and 420b engage notches (not shown) in slots 422a and 422b to secure the catheter to the collection container 430. In addition, the locking tabs 420a and 420b may produce an audible indication to the user that the tabs have been fully inserted into the slots 422a and 422b and that the connection is secure. In one embodiment, a ball valve 424 is positioned in the connector housing 416 that rotates between a sealed position when the body 12 is separated from the collection container 430 and an unsealed position when the body 12 is secured to the collection container 430. The catheter connector 426 and the collection container housing 410 may also include one or more grips 440 to facilitate use. In addition, the connector housing 416 may include one or more integrated ports, as shown in FIG. 12. Thus, for example, a first port 442 may be in fluid communication with the irrigation/sampling lumen 38, a second port 444 may be in fluid communication with inflation lumen 36, and a third port 446 may be in fluid communication with the flush lumen 44. The collection container 430 includes a rigid, curved handle 450 affixed to and extending from a top thereof, which may aid a user in carrying the collection container 430 for disposal and/or serving as a hook to quickly and easily hang the collection container 430 from a patient's bed.

Figure 13A:
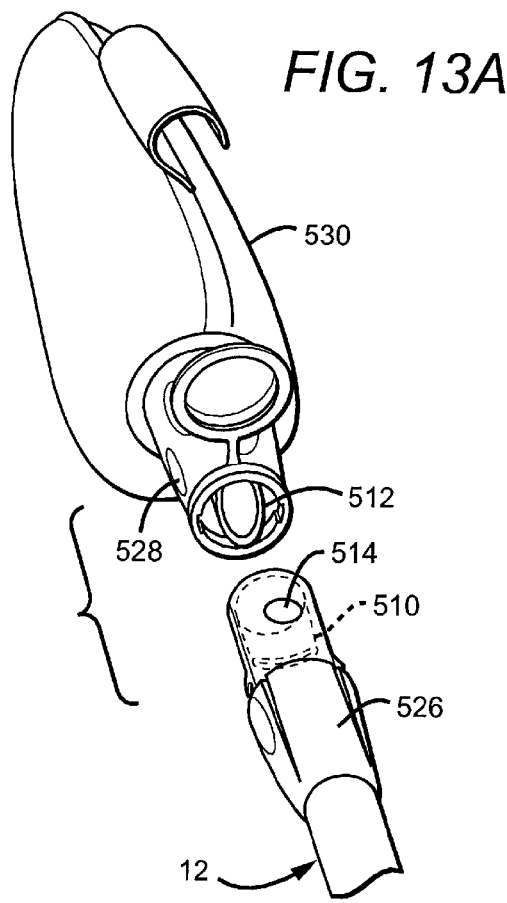
FIGS. 13A-C are perspective view of another embodiment of a connection system for a waste management system.
Figure 13B:
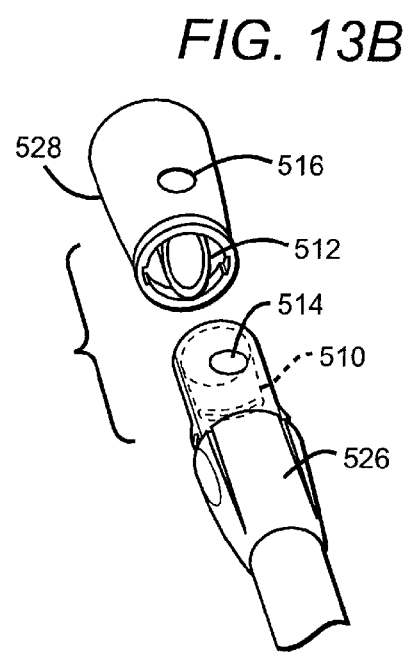
Figure 13C:
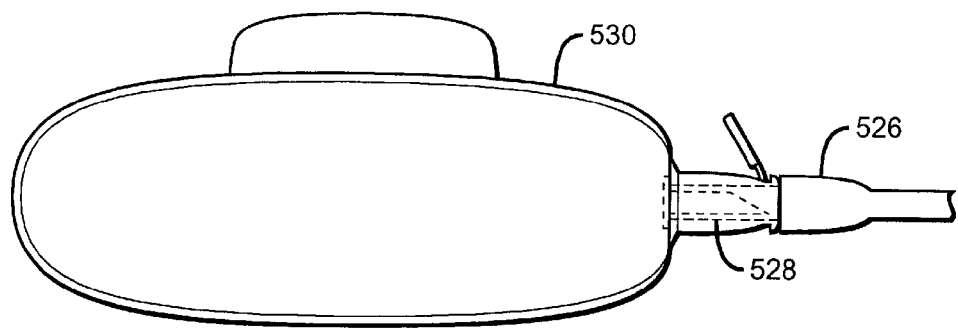

FIGS. 13A-13C illustrate an embodiment of a connection system similar to that of FIG. 12. In this embodiment, a body connector 526, coupled to the body 12, includes a duckbill valve 510 and a container connector 528 includes a concentric tube 512 with an angled face that is configured to force the valve 510 open upon contact therewith. The duckbill valve 510 is sealed when the body 12 is separated from the collection container 530 and opens as the end of the body connector 526 is inserted into the container connector 528. In one embodiment, a visual indicator is provided with the connection system to indicate a proper and secure attachment of the body connector 526 to the container connector 528. In the example of FIG. 13, best seen in FIG. 13B, an indicator 514 (e.g., a raised surface, a symbol or geometric figure with a different color than the surface on which it is placed, etc.) is located on a surface of the reduced diameter section 524 of the body connector 526. A complementary feature on the container connector 528, such as an aperture 516 with the same shape as the indicator 514, provides confirmation to the user of a secure connection when the indicator 514 is fully visible through the aperture 516.

Figure 14A:
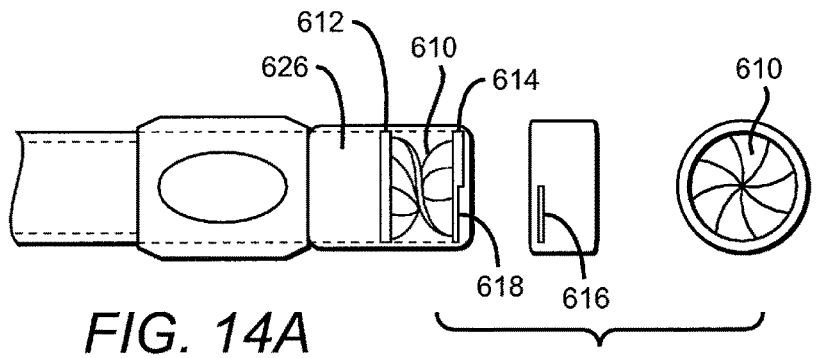
FIGS. 14A-D are perspective views of still another embodiment of a connection system for a waste management system.
Figure 14B:
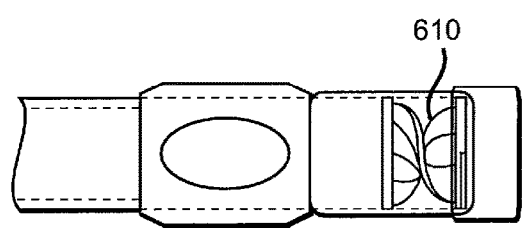
Figure 14C:
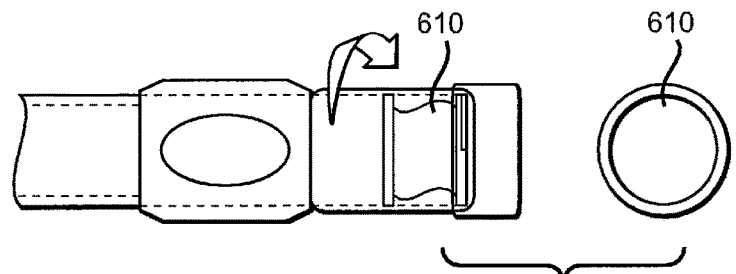
Figure 14D:
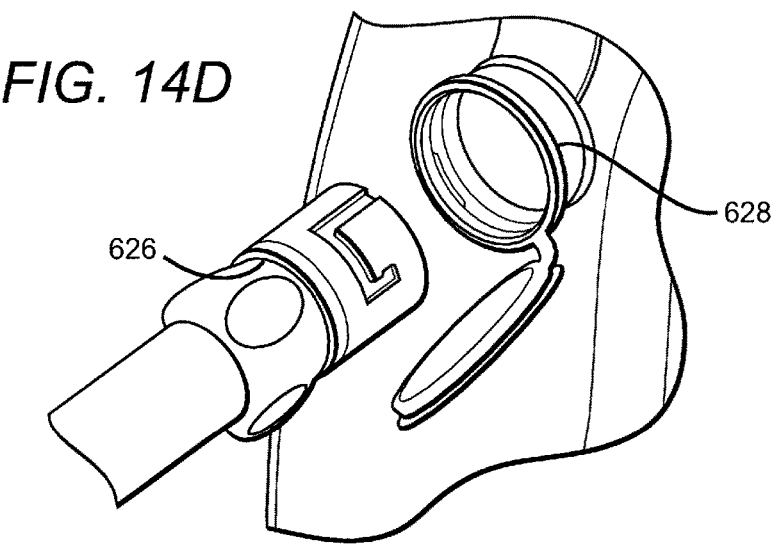

Another example of a connection system is shown in FIGS. 14A-D. A cylindrically shaped body connector 626 includes a flexible tube 610 positioned inside a channel. A first annular ring 612 is affixed to a distal end of the flexible tube 610 and to the interior wall of the body connector 626. A second annular ring 614 is affixed to a proximal end of the flexible tube 610 and is rotatably held in body connector 626. As shown in FIG. 14A, the flexible tube 610 is biased in a twisted position to seal the proximal opening of the body 12. In order to open the proximal opening, the tube 610 is untwisted as shown in FIG. 14C. Untwisting the tube 610 is accomplished by first inserting the end of the body connector 626 into the container connector 628 of a collection container (FIG. 14D) such that a tab 616 of the container connector 628 is positioned inside a corresponding slot 618 on the body connector 626, located on the second annular ring 614 (FIG. 14A). Next, the end of the body connector 626 is rotated, causing the second annular ring 614 and the proximal end of the flexible tube 610 to also rotate, thereby unsealing the opening of the body 12. Various suitable connection mechanisms can be used to secure the catheter connector 626 to the container connector 628. For example, FIG. 14D shows a bayonet style connection mechanism that gives positive feedback to the user when connection is complete. In addition, the collection container opening can be sealed by various suitable mechanisms, including a standard ostomy bag flap as discussed above.

Turning now to FIGS. 15A-15D, one embodiment of an insertion device for a waste management system is illustrated. The insertion device 700 is configured to facilitate insertion of a waste transport device. Insertion device 700 includes an inner sleeve 702 and an outer sleeve 704, each having a generally tubular configuration and flanges at a proximal end thereof. The outwardly extending flanges of the outer sleeve 704 are configured to prevent over-insertion of the device 700, indicating to a user that maximum safe insertion has been reached when the flanges are adjacent a patient's buttocks. The outwardly extending flanges of the inner sleeve 702 provide an indication to the user that the retention cuff has moved distally through the distal end of the outer sleeve 704 when the outer sleeve flanges are adjacent thereto. The proximal end of both the inner sleeve 702 and the outer sleeve 704 include respective pairs of c-rings 706a, 706b and 708a, 708b positioned on the respective flanges. Each pair of c-rings 706a, 706b and 708a, 708b are separated by a pair of v-cuts 710 and 712 (only one side of v-cuts shown in FIG. 15A). The v-cuts 710 and 712 facilitate disassembly of the sleeves 702 and 704 from the body 12 post insertion, as the v-cuts feed into a split section (e.g., an elongate score from the v-cut to the distal end of the sleeve) that separates the sleeve into two pieces. The insertion device 700 is shown on the body 12 in an insertion configuration in FIG. 15B, a distal end of the outer sleeve 704 covering the rectal section 18, the retention cuff 24 held by the outer sleeve 704 in its collapsed configuration. In one embodiment, the outer sleeve 704 is configured to compress the retention cuff 24 in order to provide a lower profile for the device 700.

Figure 15A:
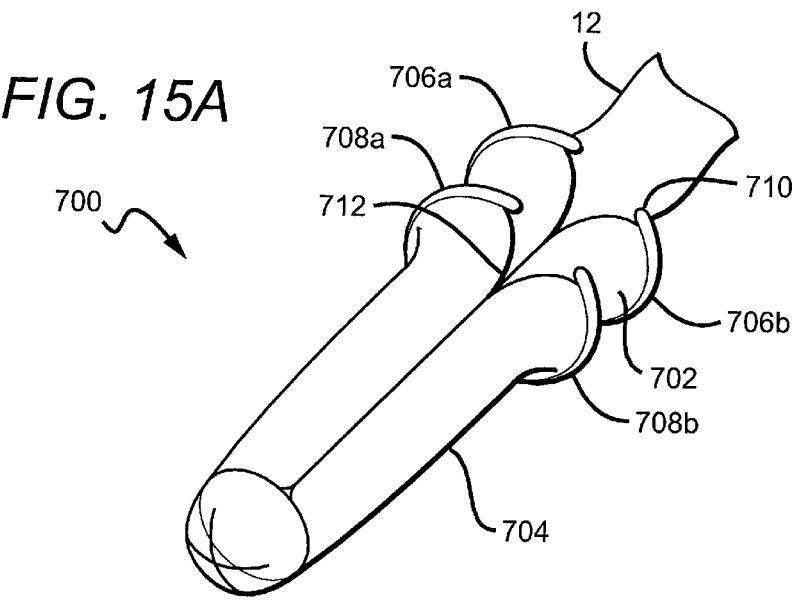
FIGS. 15A-D are perspective views of one embodiment of an insertion device for a waste management system.
Figure 15B:
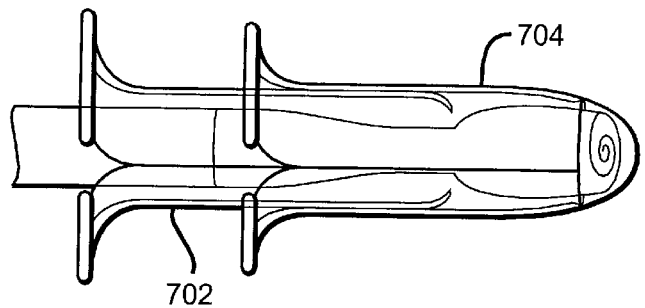
Figure 15C:
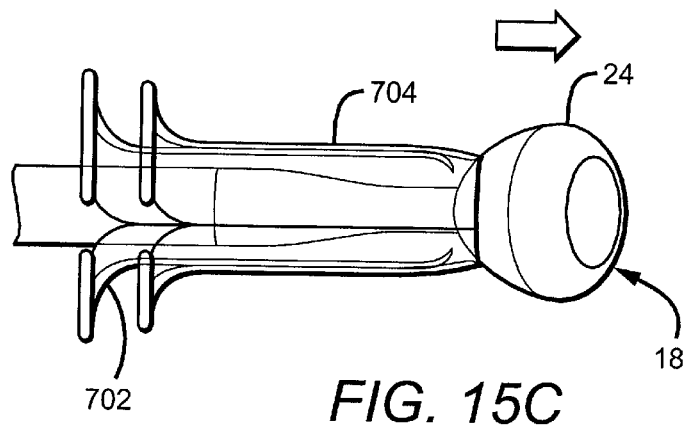
Figure 15D:
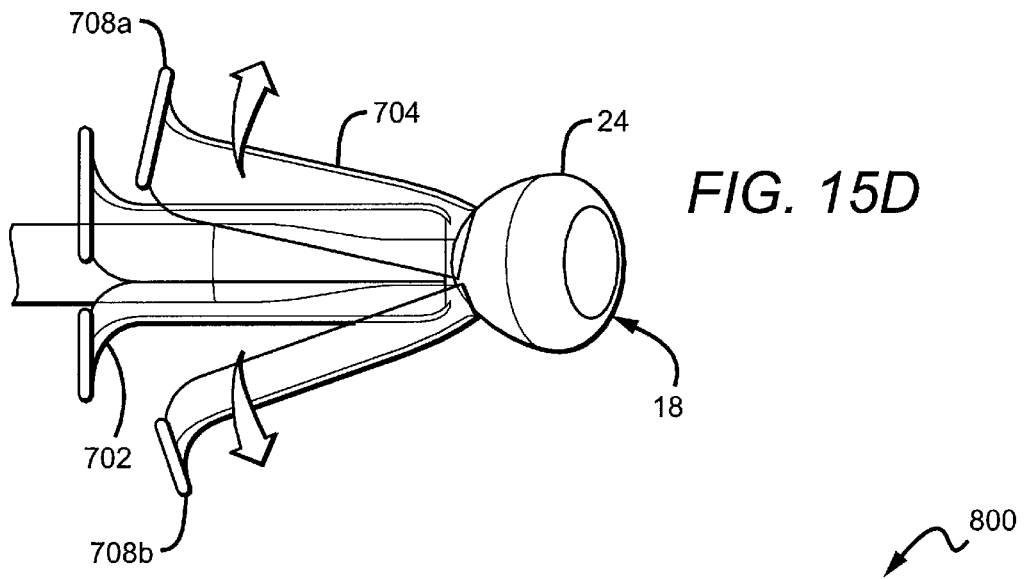

FIG. 15C shows the insertion device 700 as it is retracted from the rectal section 18, the end of the outer sleeve having a perforated section to permit passage of the rectal section 18 therethrough. Retraction of the outer sleeve 704 may occur during insertion due to forces acting on the insertion device 700 or may be manually performed by a user following insertion. FIG. 15D shows retraction of the outer sleeve 704 and initial removal of the insertion device 700 from the body 12. It should be noted that the retention cuff may self-expand following retraction of the outer sleeve 704 in some embodiments, and in others will require inflation. Following proper positioning of the body 12 in the patient, the insertion device 700 can be disassembled by grasping the pair of c-rings 708a and 708b and pulling the outer sleeve 704 apart along its v-cuts 712, and then grasping inner sleeve 702 in a similar manner and pulling apart and off of the body 12. Removal of the device 700 may occur after only a portion of the outer sleeve 704 is retracted from the rectal section 18 or after the device 700 is slid proximally further along the body 12.

Figure 16A:
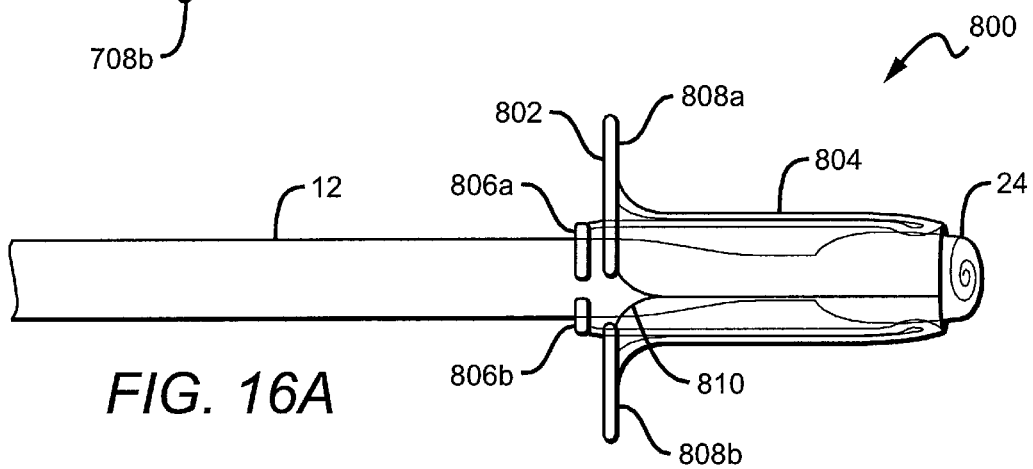
FIGS. 16A-C are perspective views of another embodiment of an insertion device for a waste management system.
Figure 16B:
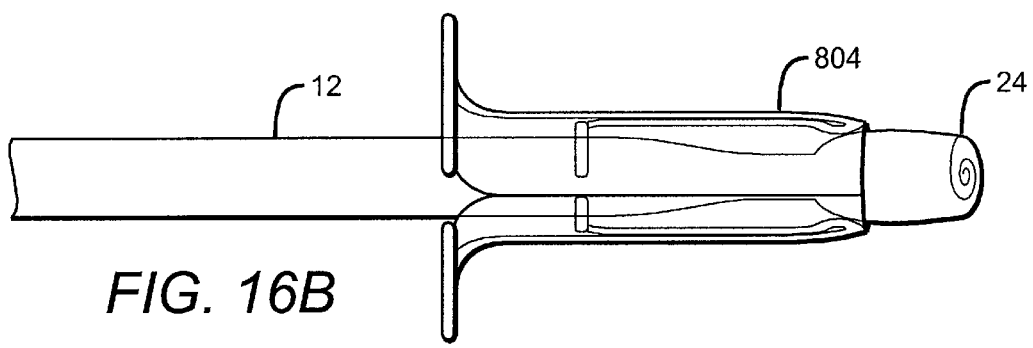
Figure 16C:
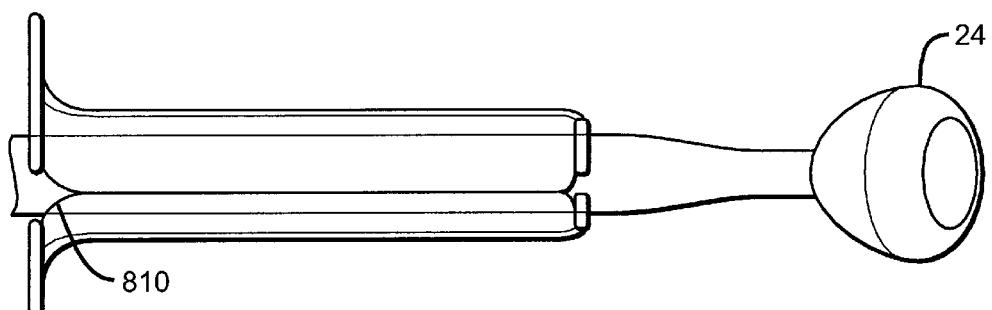
Figure 17A:
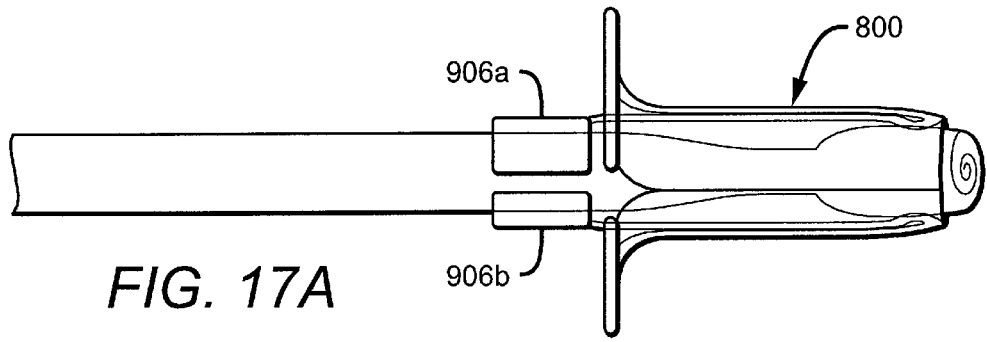
FIGS. 17A-D are perspective views of another embodiment of an insertion device for a waste management system.
Figure 17B:
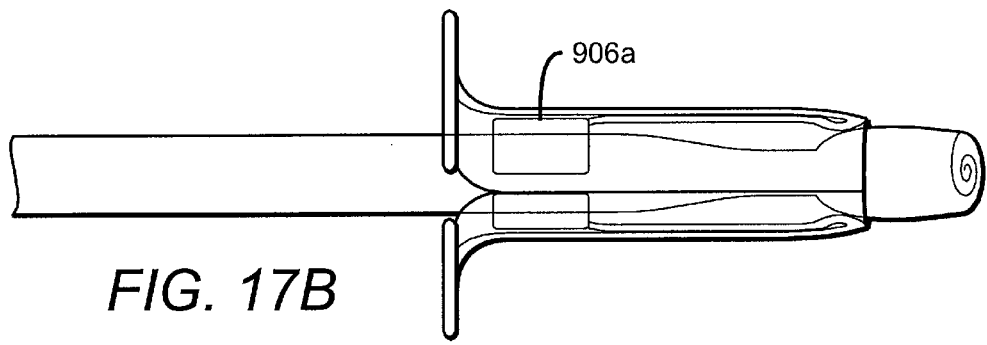
Figure 17C:
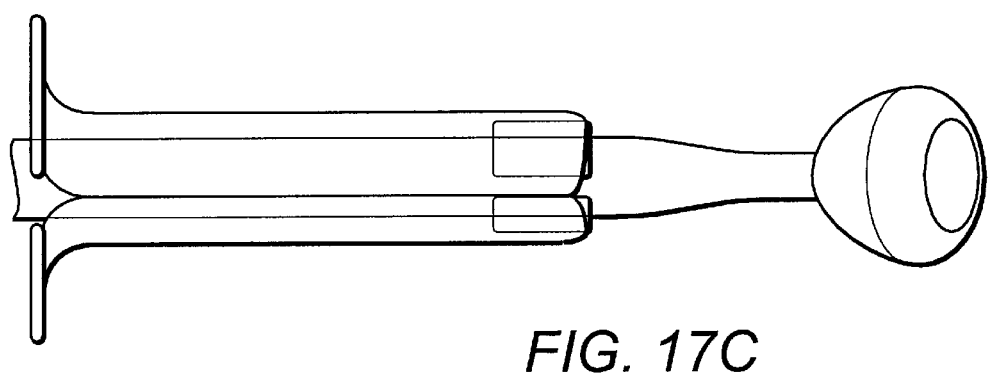
Figure 17D:
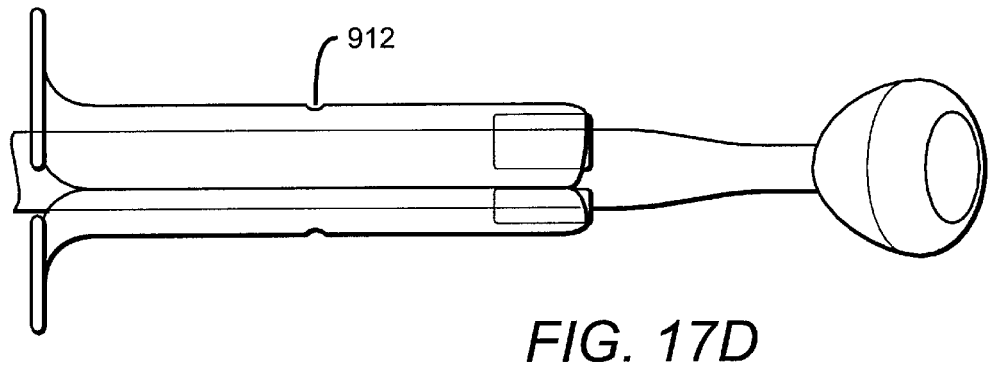

Another embodiment of an insertion device is illustrated in FIGS. 16A-C. The insertion device 800 includes a disposable sleeve with an outer portion 804 folded over an inner portion 802 in a rolling diaphragm arrangement. The inner portion 802 may have a suitable adhesive disposed on an inner surface thereof to prevent migration of the device 800 during insertion. A first end of the sleeve, initially inner portion 802, includes a pair of inner cuff rings 806a and 806b, while a second end of the sleeve, initially outer portion 804, includes a pair of outer cuff c-rings 808a and 808b. FIG. 16A shows the device 800 in an insertion position with the retention cuff 24 folded and held in a folded state by sleeve outer portion 804. To deploy the waste transport device in the patient, the outer portion 804 is pulled in a proximal direction, as shown in FIG. 16B, until fully pulled from over the inner portion 802, as shown in FIG. 16C. In this position, the retention cuff 24 is released from its folded position and allowed to expand and/or inflated. The insertion device 800 is removed by pulling the c-rings 808a and 808b apart so that the v-cuts 810 expand, separating the sleeve into two pieces, and pulling away from the body 12. FIGS. 17A-17D illustrate a variation of device 800 with inner cuffs 906a and 906b that have a longer length than cuffs 806a and 806b. The length of the cuffs (e.g., in the range of about 1 inch to about 2 inches) provides clamping to prevent migration, thereby potentially eliminating the need for an adhesive on the inner surface of the inner portion 804. In one embodiment, the insertion device 800 includes dimpled c-rings to help a user load the catheter correctly. In another embodiment, a reduced diameter section 912 is included where the inner portion 802 and outer portion 804 of the sleeve meet when in the insertion position. As shown in FIG. 17D, when the outer portion is pulled in the proximal direction, the reduced diameter section 912 may indicate to a user when the insertion device 800 is fully unrolled to the correct point of insertion. The reduced section 912 also provides a narrower entry for the device 800 at the insertion point.

Figure 18A:
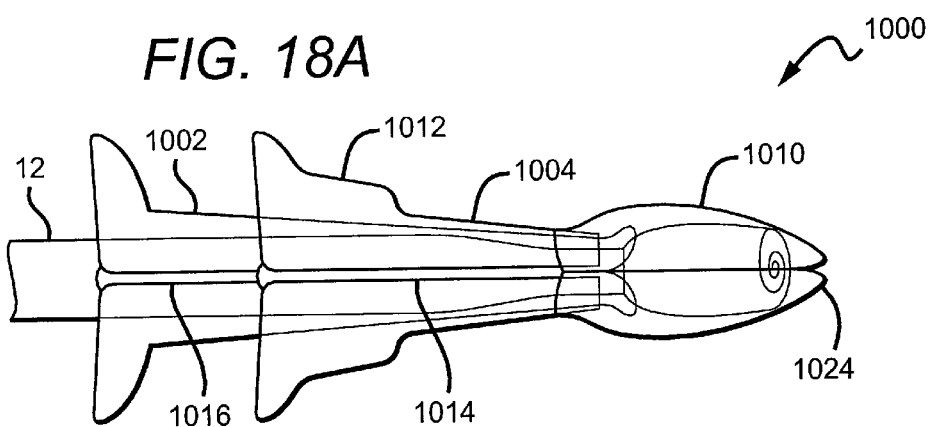
FIGS. 18A-C are perspective views of yet another embodiment of an insertion device for a waste management system.
Figure 18B:
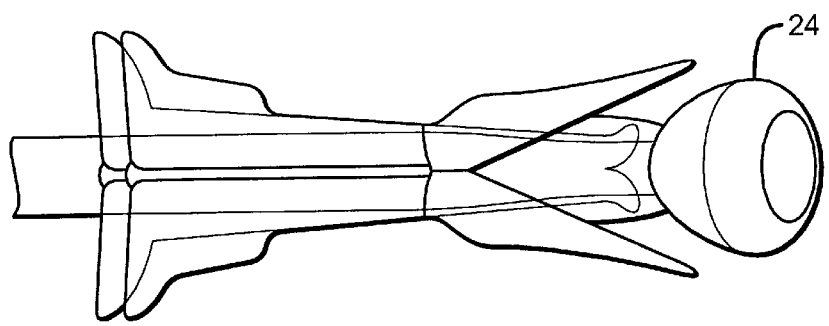
Figure 18C:
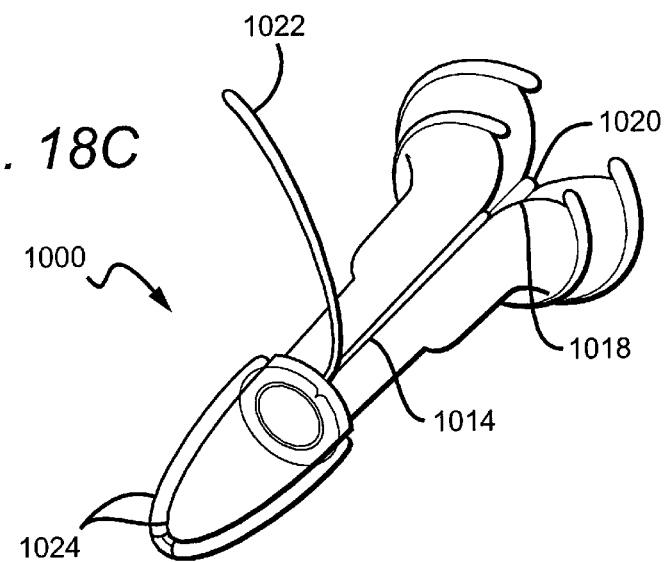

Another embodiment of an insertion device is illustrated in FIGS. 18A-18C. Insertion device 1000 includes a separate inner sleeve 1002 and outer sleeve 1004, similar to the embodiments of FIG. 15. In this embodiment, a distal end of the outer sleeve 1004 includes a tapered head 1010 to facilitate insertion by providing a smaller profile. The tapered head 1010 can also provide a smooth transition from the sphincter section 20 of the catheter and can be constructed of a flexible material with rounded edges to minimize discomfort. In addition, the insertion device 1000 can include an increased diameter limiter flange 1012 extending from a proximal end of the outer sleeve 1004. The limiter flange 1012 can be configured to assist a user to locate a proper insertion depth. For example, the limiter flange 1012 can be set at a predetermined distance along the insertion device 1000 so that a person administering the body 12 can use to the limiter flange 1012 as a reference as to how far the body 12 is inserted into the patient. The limiter flange 1012 can also limit the depth that that the insertion device 1000 can be inserted into the patient. FIG. 18B shows the insertion device 1000 in a retracted configuration with the rectal section 18 with retention cuff 24 released and expanded. As the outer sleeve 1004 is retracted, the head 1010 of the insertion device 1000 splits apart at a plurality of tear away seams 1024 to permit relative distal movement of the body 12.

The insertion device 1000 is removed from the body 12 by pulling the outer sleeve 1002 and inner sleeve 1004 apart at tear zones 1014 and 1016, respectively, that begin with corresponding v-cuts 1018 and 1020. In one embodiment, the insertion device 1000 includes one or more "rip strips" to facilitate disassembly of the insertion device 1000. An exemplary rip strip 1022, shown pulled away from the outer sleeve 1004, is illustrated in FIG. 18C. One or more rip strips may also be included on the inner sleeve 1002.

Yet another embodiment of an insertion device 1100 is illustrated in FIGS. 19A-C. In this embodiment, the insertion device 1100 utilizes a scissor action similar to that of a disposable vaginal speculum. A catheter, such as body 12, has a plunger 1102 disposed about a distal portion thereof, the plunger 1102 including a pair of grips 1104*a* and 1104*b* extending from its proximal end configured for removing the plunger 1102 following insertion of the body 12 in the patient. A scissor device 1106 includes a rigid upper arm 1108 and a rigid lower arm 1110 pivotally connected to one another at pivot point 1112. A soft, flexible sleeve 1114 is positioned around an upper portion of the scissor device 1106, which covers the pinch points of the scissor device 1106 and provides a protective cover for at least a portion of the body 12 and/or plunger 1102 during insertion. As shown in FIG. 19B, squeezing handles 1116 and 1118 together causes the pivotal movement of the upper arm 1108 away from the lower arm 1110, which may be limited by the sleeve 1114. For insertion, the distal portion of the body 12 and plunger 1102 are inserted into a proximal opening of the scissor device 1106, either before or after the scissor device 1106 is inserted into a patient. The handles of the device 1106 are then squeezed together to facilitate insertion of the body into the patient. The plunger grips 1104*a*, 1104*b* extend outward from the plunger and may be spaced from a distal end of the body 12 to indicate to the user a proper depth of insertion or to indicate the maximum safe depth of insertion when the grips 1104*a*, 1104*b* come into contact with a proximal end of the device 1106. One or more tear-away bands may be included on the plunger 1102 to facilitate removal.

Still another embodiment of an insertion device is illustrated in FIGS. 20A-20C. Insertion device 1200 includes an upper sleeve 1202 attached along one or more tear away seams 1210 to a lower sleeve 1204. A spacer 1212 is provided to indicate proper or safe insertion depth of the device. A handle 1214 is provided at the proximal end of the lower sleeve 1204 to facilitate handling and insertion. The upper sleeve 1202 in one embodiment is made of a material that more flexible than the lower sleeve 1204. In the insertion configuration shown in FIG. 20A, the insertion device 1200 compresses the folded retention cuff 24 to provide a lower profile for easier insertion into the patient. Following insertion, the device 1200 is removed by first shearing back the upper sleeve 1202, as shown in FIG. 20B, which splits a tip 1206 to expose the retention cuff 24 and allow it to expand (e.g., unfold). Then, the upper sleeve 1202 is removed from the patient, as shown in FIG. 20C, followed by removal of the lower sleeve 1204.

FIG. 21 illustrates an insertion device 1300 configured similar to a sheath introducer or tampon applicator. The distal end of the body 12 is inserted into the device 1300, which may have a lubricious coating on an outer surface thereof. The distal end 1302 has a plurality of petals that together maintain the folded profile of the retention cuff 24, but which split apart when the body 12 is pushed in a distal direction to permit passage of the body therethrough. To remove, the device 1300 is slid in a proximal direction along the body. The device 1300 may also include visual depth markers and/or an anchoring mechanism.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A waste management system, comprising:
a waste transport device, including:
a collection member defining in an expanded configuration a distal end opening having a first cross-sectional area and a proximal end opening having a second cross-sectional area less than the first cross-sectional area, a passage connecting the distal end opening and the proximal end opening tapering from the first cross-sectional area to the second cross-sectional area;
a retention cuff disposed about an outer surface of the collection member; and
a first section having a lumen in fluid communication with a lumen of the collection member; and
a waste collection device.

2. The system according to claim 1, wherein the first section has a cross-sectional shape at a proximal end different from a cross-sectional shape at a distal end.

3. The system according to claim 2, wherein the cross-sectional shape at the proximal end is circular and the cross-sectional shape at the distal end is oval.

4. The system according to claim 1, wherein the first section has an hourglass-shaped configuration.

5. The system according to claim 1, wherein the collection member and the first section are formed together into a single member.

6. The system according to claim 5, wherein a distal end of the single member is folded over at the collection member distal end opening to form a rolling portion, the retention cuff attached to the rolling portion.

7. The system according to claim 5, further comprising a placement tool including an end piece with a cross-sectional area similar to the second cross-sectional area.

8. The system according to claim 7, wherein the placement tool end piece has a greater rigidity than a rigidity of the collection member, the end piece collapsing the collection member from the first cross-sectional area to the second cross-sectional area upon movement along the collection member toward the rolling portion.

9. A waste management system, comprising:
a waste transport device, including:
a collection member defining in an expanded configuration a distal end opening having a first cross-sectional area and a proximal end opening having a second cross-sectional area less than the first cross-sectional area, a passage connecting the distal end opening and the proximal end opening tapering from the first cross-sectional area to the second cross-sectional area;
a retention cuff disposed about an outer surface of the collection member; and
a first section having a distal end connected to a proximal end of the collection member; and
a waste collection device.

10. The system according to claim 9, wherein the first section has a wall thickness less than a wall thickness of the collection member.

11. The system according to claim 9, wherein the first section includes a material different from a material of the collection member.

12. The system according to claim 9, wherein a proximal end of the first section has a circular cross-sectional shape and the distal end of the first section has an oval cross-sectional shape.

13. The system according to claim 9, wherein the first section includes a plurality of inflatable ribs or rings.

14. The system according to claim 9, the waste transport device further comprising a second section having a distal end connected to a proximal end of the first section.

15. The system according to claim 14, the second section including a flush lumen disposed along a length thereof.

16. The system according to claim 15, wherein the flush lumen comprises a plurality of spaced apart apertures along a length thereof.

17. A waste transport device, comprising:
a distal section defining in an expanded configuration a distal end opening having a first cross-sectional area and a proximal end opening having a second cross-sectional area less than the first cross-sectional area, a passage connecting the distal end opening and the proximal end opening tapering from the first cross-sectional area to the second cross-sectional area, the distal section including an inflatable retention cuff;
a proximal section including a flush lumen, a connector coupled to a proximal end of the proximal section; and
an intermediate section connecting the proximal section to the distal section, the intermediate section including a transitioning cross-sectional shape from a proximal end to a distal end.

18. The device according to claim 17, wherein the intermediate section has an oval cross-section at the proximal end and a circular cross-section at the distal end.

19. The device according to claim 17, further comprising an inflation lumen in fluid communication with the inflatable retention cuff and a sampling lumen having a distal end adjacent the distal end opening of the distal section.

20. The device according to claim 17, wherein the flush lumen includes a plurality of apertures spaced apart along a longitudinal axis of the proximal section.

\* \* \* \* \*